US010758431B2

(12) United States Patent
Splendiani et al.

(10) Patent No.: US 10,758,431 B2
(45) Date of Patent: Sep. 1, 2020

(54) FORMED FILMS AND APPARATUS FOR MANUFACTURING THE SAME

(71) Applicant: TREDEGAR FILM PRODUCTS LLC, N. Chesterfield, VA (US)

(72) Inventors: Antonietta Splendiani, Glen Allen, VA (US); Brian C. Loomis, Terre Haute, IN (US); John Richard Renner, Marshall, IL (US); Todd R. Skochdopole, Moseley, VA (US)

(73) Assignee: TREDEGAR FILM PRODUCTS LLC, N. Chesterfiel, VA (US)

( * ) Notice: Subject to any disclaimer, the term of this patent is extended or adjusted under 35 U.S.C. 154(b) by 470 days.

(21) Appl. No.: 15/584,968

(22) Filed: May 2, 2017

(65) Prior Publication Data

US 2017/0312143 A1 Nov. 2, 2017

Related U.S. Application Data

(60) Provisional application No. 62/369,624, filed on Aug. 1, 2016, provisional application No. 62/330,589, filed on May 2, 2016.

(51) Int. Cl.
*A61F 13/514* (2006.01)
*A61F 13/512* (2006.01)
(Continued)

(52) U.S. Cl.
CPC ............ *A61F 13/514* (2013.01); *A61F 13/15* (2013.01); *A61F 13/15707* (2013.01);
(Continued)

(58) Field of Classification Search
CPC .. A61F 13/15; A61F 13/15707; A61F 13/511; A61F 13/51104; A61F 13/512;
(Continued)

(56) References Cited

U.S. PATENT DOCUMENTS 4,327,730 A * 5/1982 Sorensen .............. A61F 13/512
428/131
4,395,215 A 7/1983 Bishop
(Continued)

FOREIGN PATENT DOCUMENTS

EP 0057483 A2 11/1982
EP 1510192 A2 3/2005
(Continued)

OTHER PUBLICATIONS

International Search Report and Written Opinion dated Sep. 8, 2017, for International Patent Application No. PCT/US2017/30644.
(Continued)

*Primary Examiner* — Adam Marcetich
(74) *Attorney, Agent, or Firm* — Karceski IP Law, PLLC

(57) ABSTRACT

A formed film includes a first surface generally located in a first plane, a second surface generally located in a second plane parallel to and spaced from the first plane, and a third surface generally located in a third plane parallel to and spaced from the first plane and the second plane, in between the first plane and the second plane. A porous structure extends between the second surface and the third surface. A plurality of raised areas have sidewalls that extend between the first surface and the third surface, and top portions that define the first surface. The plurality of sidewalls, the porous structure, and the first plane define a plurality of gathering volumes.

16 Claims, 28 Drawing Sheets

(51) Int. Cl.
*A61F 13/15* (2006.01)
*A61F 13/511* (2006.01)
*A61F 13/513* (2006.01)
*A61L 15/42* (2006.01)

(52) U.S. Cl.
CPC .......... *A61F 13/511* (2013.01); *A61F 13/512* (2013.01); *A61F 13/513* (2013.01); *A61F 13/5121* (2013.01); *A61F 13/5122* (2013.01); *A61F 13/51104* (2013.01); *A61L 15/42* (2013.01)

(58) Field of Classification Search
CPC .............. A61F 13/5121; A61F 13/5122; A61F 13/513; A61F 13/514; A61L 15/42
See application file for complete search history.

(56) References Cited

U.S. PATENT DOCUMENTS

| | | | |
|---|---|---|---|
| 4,601,868 A | | 7/1986 | Radel et al. |
| 4,637,819 A | | 1/1987 | Oullette et al. |
| 4,704,112 A | | 11/1987 | Suzuki et al. |
| 5,158,819 A | * | 10/1992 | Goodman, Jr. ... A61F 13/15731 428/131 |
| 5,567,376 A | * | 10/1996 | Turi ................. A61F 13/15731 264/455 |
| 5,895,380 A | * | 4/1999 | Turi ................. A61F 13/47218 604/383 |
| 5,980,814 A | * | 11/1999 | Roller ............... A61F 13/00991 264/455 |
| 5,989,478 A | | 11/1999 | Ouellette et al. |
| 5,998,696 A | * | 12/1999 | Schone ............. A61F 13/5122 604/368 |
| 6,228,462 B1 | * | 5/2001 | Lee .................... A61F 13/512 428/131 |
| 6,242,074 B1 | * | 6/2001 | Thomas ........... A61F 13/15577 428/137 |
| 6,461,716 B1 | * | 10/2002 | Lee ........................ A61L 15/26 428/137 |
| 6,517,925 B1 | * | 2/2003 | Hisanaka .......... A61F 13/15707 428/131 |
| 2002/0133132 A1 | * | 9/2002 | Copat ............... A61F 13/15731 604/383 |
| 2003/0201582 A1 | * | 10/2003 | Gray ................. A61F 13/51104 264/504 |
| 2004/0122395 A1 | | 6/2004 | Stone et al. |
| 2004/0161586 A1 | * | 8/2004 | Cree ..................... B32B 37/153 428/131 |
| 2004/0247833 A1 | * | 12/2004 | Copat .............. A61F 13/15731 428/156 |
| 2005/0049567 A1 | * | 3/2005 | Cree ................. A61F 13/15203 604/378 |
| 2006/0019063 A1 | * | 1/2006 | Kelly ................... A61F 13/537 428/131 |
| 2007/0255247 A1 | | 11/2007 | Moberg-Alehammar et al. |
| 2008/0206529 A1 | * | 8/2008 | Ueminami ........... A61F 13/512 428/196 |
| 2009/0182295 A1 | * | 7/2009 | Seyler ............... A61F 13/53747 604/378 |
| 2012/0095426 A1 | | 4/2012 | Visscher et al. |
| 2013/0281950 A1 | * | 10/2013 | Digiacomantonio ........................ A61F 13/511 604/366 |
| 2014/0087130 A1 | | 3/2014 | Seyler et al. |
| 2014/0121623 A1 | | 5/2014 | Kirby et al. |
| 2014/0296815 A1 | * | 10/2014 | Takken ............. A61F 13/51104 604/383 |
| 2015/0038933 A1 | | 2/2015 | Day et al. |
| 2015/0273793 A1 | * | 10/2015 | Thomas ........... A61F 13/15731 428/178 |
| 2016/0038351 A1 | * | 2/2016 | Cecchetto ........... A61F 13/5121 428/134 |
| 2016/0067118 A1 | | 3/2016 | Hammons et al. |

FOREIGN PATENT DOCUMENTS

| | | |
|---|---|---|
| EP | 1574324 A1 | 9/2005 |
| WO | 2015146717 A1 | 10/2015 |
| WO | WO-2016172929 A1 * 11/2016 | ............. D04H 1/593 |

OTHER PUBLICATIONS

International Preliminary Report on Patentability dated Nov. 6, 2018, for International Patent Application No. PCT/US2017/030644.
Extended European Search Report dated Dec. 10, 2019, for European Patent Application No. 17793164.9.

* cited by examiner

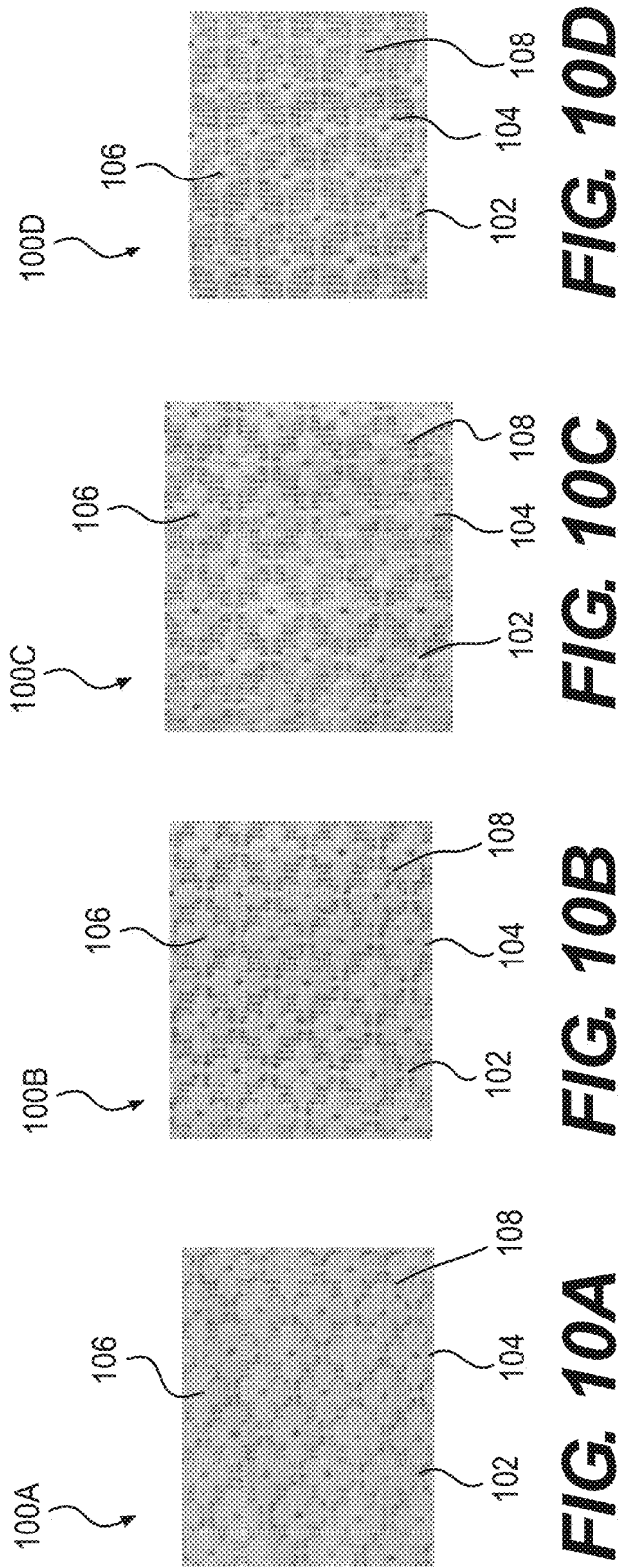

FORMED FILMS AND APPARATUS FOR MANUFACTURING THE SAME

CROSS-REFERENCE TO RELATED APPLICATIONS

This application claims the benefit of priority from U.S. Provisional Patent Application Ser. No. 62/330,589, filed on May 2, 2016, and U.S. Provisional Patent Application Ser. No. 62/369,624, filed Aug. 1, 2016, the entire contents of both of which are incorporated herein by reference.

FIELD OF THE INVENTION

The present invention is related to formed films and an apparatus for manufacturing the formed films. The formed films of the present invention may be used in absorptive end-products for the transmission of fluids.

BACKGROUND OF THE INVENTION

Formed films are used in end-products such as absorbent articles, including feminine hygiene products, adult incontinence products, and baby diapers, for example. One type of formed film that may be used in such products is a so-called topsheet, which is a top layer of the end-product that contacts the skin of the user (wearer) of the end-product. It is desirable for a topsheet that is made from a plastic film to have the visual appearance and softness of a soft cloth, instead of a stiff plastic film. However, trade-offs exist between achieving softness and a pleasant visual appearance (e.g. pattern visibility, low gloss, etc.), and the convertibility of the topsheet into the end-product, as well as the performance of the topsheet (e.g. surface distribution, wetness, masking, rewet, etc.) in the end-product when worn by the user.

The visual appearance of a topsheet, including the patterns and sizes of apertures, is generated by "thermal" forming or thermoforming, which may include vacuum-forming, hydro-forming, embossing, mechanical perforating, etc., of a web of material. In vacuum-forming and hydro-forming processes, a web is deposited on a rotating forming structure, such as a screen, that includes openings corresponding to a desired pattern. In a vacuum-forming process, a relative vacuum is established across the forming structure so that the web is drawn into the openings, thereby forming a series of protrusions on the film surface. If the vacuum differential is sufficient, an opening such as a micro-aperture, may be formed in the web at the apex of each protrusion. In a hydro-forming process, similar protrusions/micro-apertures may be formed by directing a high pressure water stream at the side of the web that is opposite the forming structure. The pressure of the water stream forces the web into the opening of the forming structure. If sufficient pressure is applied, an aperture is formed in the web at the apex of each protrusion. Apertures may also be formed using mechanical methods such as needle punching, but such methods may require additional steps to provide the three dimensionality that tends to enhance the perceived softness of the final film.

A visual appearance that is appealing to users is traditionally generated by a large hydraulic radius, which should also promote absorption, and consequently a relatively high caliper or thickness, which may make the film more difficult to convert into the final end-product. Softness may be generated by softer polymers, flexible micro-structures, and cushioning structures. However, forming the webs of materials at high temperatures may make the resulting films stiffer and less soft. Conversely, softer films tend to be more difficult to convert into the final product.

In general, topsheets that are made from plastic films have better performance characteristics when used in the end-product as compared to topsheets that are made from non-woven materials. However, a topsheet made from a plastic film may have a visual appearance that is higher in gloss and therefore may be more "plastic-looking" than a non-woven topsheet, and a plastic film topsheet may feel more "sticky" or "tacky" to the wearer than a non-woven topsheet.

Typical apertured topsheets generally create a visual appearance by thermoforming holes having round, elongated, hexagonal and/or slit shapes, but challenges exist to create a unique and effective visual appearance. On the other hand, embossed topsheets may have unique visual appearances due to the laser engraving technology that is used to generate such structures, but embossed topsheets generally have very small hydraulic radii and lower performance as compared to apertured topsheets. In addition, higher basis weights are typically needed for embossed topsheets to obtain visual appearances that are more appealing to the user.

It is desirable to create a topsheet that 1) has a unique and effective visual appearance in order to convey a promise of protection to the user, 2) delivers extraordinary softness to the user, 3) assures performance at least comparable to traditional films, and 4) is able to be converted into the end-product on conventional equipment.

SUMMARY OF THE INVENTION

It is an aspect of the present invention to provide a formed film that includes a first surface generally located in a first plane, a second surface generally located in a second plane parallel to and spaced from the first plane, and a third surface generally located in a third plane parallel to and spaced from the first plane and the second plane, in between the first plane and the second plane. A porous structure extends between the second surface and the third surface, and a plurality of raised areas have sidewalls that extend between the first surface and the third surface, and top portions that define the first surface. The plurality of sidewalls, the porous structure and the first plane define a plurality of gathering volumes.

In an embodiment, the plurality of raised areas include a plurality of micro-apertures. In an embodiment, the micro-apertures are arranged in a 40 to 120 mesh pattern. In an embodiment, the micro-apertures are arranged in an 80 mesh pattern. In an embodiment, the micro-apertures are arranged in a 100 mesh pattern.

In an embodiment, a distance between the first plane and the second plane is between about 500 µm and about 1200 µm. In an embodiment, the distance between the first plane and the second plane is between about 500 µm and about 1000 µm. In an embodiment, the distance between the first plane and the second plane is between about 600 µm and about 900 µm.

In an embodiment, the porous structure includes a fibrillated structure.

In an embodiment, the raised areas are ridges. In an embodiment, the ridges are generally straight. In an embodiment, the ridges are generally curved. In an embodiment, the raised areas form a plurality of spirals.

In an embodiment, the formed film comprises three layers, including a core layer and two skin layers on opposite sides of the core layer.

In an embodiment, the gathering volumes are pockets. In an embodiment, the gathering volumes are channels.

According to an aspect of the present invention, there is provided an absorbent article that includes a topsheet configured to contact skin of a user of the absorbent article when the absorbent article is worn by the user. The topsheet includes a formed film and the formed film includes a first surface generally located in a first plane, a second surface generally located in a second plane parallel to and spaced from the first plane, and a third surface generally located in a third plane parallel to and spaced from the first plane and the second plane, in between the first plane and the second plane. A porous structure extends between the second surface and the third surface, and a plurality of raised areas have sidewalls that extend between the first surface and the third surface, and top portions that define the first surface. The plurality of sidewalls, the porous structure and the first plane define a plurality of gathering volumes. The absorbent article includes a liquid impervious backsheet configured to be in contact with a garment worn by the user, and an absorbent core positioned in between the topsheet and the backsheet.

In an embodiment, the absorbent article includes a sublayer positioned in between the topsheet and the absorbent core.

According to an aspect of the present invention, there is provided an apparatus for manufacturing a formed film. The apparatus includes a first forming station configured to receive a polymer web. The first forming station has a first forming structure that includes a plurality of first openings configured to form a plurality of apertures in the polymer web. The apparatus includes a second forming station configured to receive the polymer web from the first forming station after the polymer web has been apertured. The second forming station includes a second forming structure that includes a plurality of second openings and an overlying pattern configured to form raised areas in the polymer web to create a three-dimensional formed film.

In an embodiment, the plurality of first openings are arranged in a 40 to 120 mesh pattern.

In an embodiment, the plurality of second openings are arranged in a 40 mesh pattern.

In an embodiment, the overlying pattern configured to form raised areas includes a spiral pattern.

These and other aspects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

BRIEF DESCRIPTION OF THE DRAWINGS

The components of the following figures are illustrated to emphasize the general principles of the present disclosure and are not necessarily drawn to scale. Reference characters designating corresponding components are repeated as necessary throughout the figures for the sake of consistency and clarity.

FIGS. 10A-10D are top views of portions of formed films according to embodiments of the present invention;

DETAILED DESCRIPTION

Figure 1:
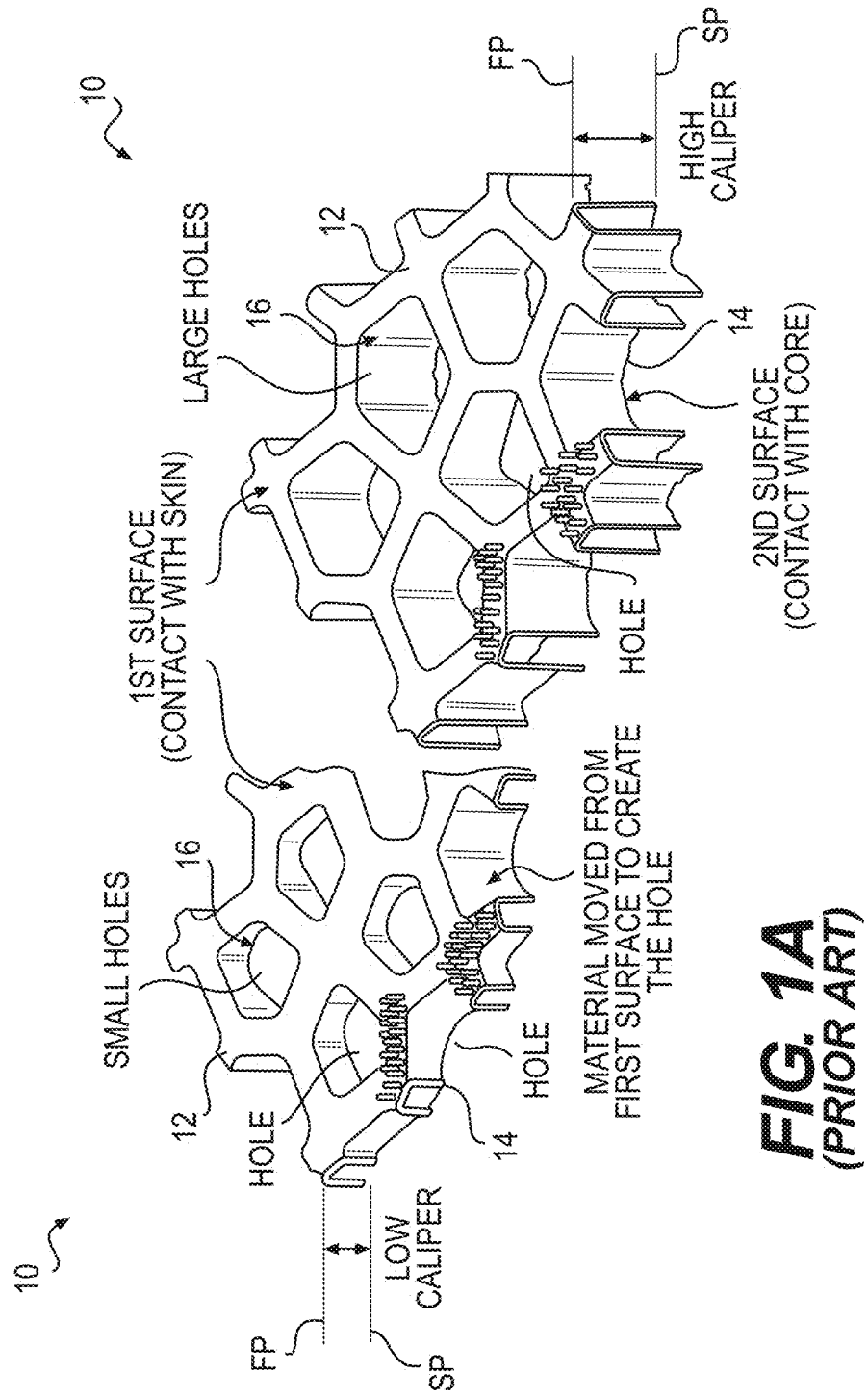
FIGS. 1A and 1B are schematic perspective views of portions of formed films of the prior art.

FIGS. 1A and 1B are schematic perspective views of portions of a formed film 10 of the prior art created with a thermoforming method of manufacture. As illustrated, the formed film 10 generally includes a first surface 12 that is generally located in a first plane FP and a second surface 14 that is generally located in a second plane SP. As illustrated, the first surface 12 is located above the second surface 14 and the second surface 14 is configured to contact a core of an end-product when converted into the end-product, such as a feminine hygiene napkin or other absorbent article. The first surface 12 of the film 10 is configured to contact the skin of the user when the user wears the end-product that includes the film 10.

A thermoforming process may be used to generate a plurality of openings 16 in the film 10 and draw portions of the film that originated in the first plane FP down towards the second plane SP, thereby creating a three-dimensional thickness (measured as the caliper of the film) between the first surface 12 and the second surface 14 of the film 10. As illustrated, as the size of the openings 16 is increased, the more material is removed from the first surface 12, which increases the thickness and caliper of the film 10. Similarly, as the size of the openings 16 is decreased, less material is removed from the first surface 12, which decreases the thickness and caliper of the film 10. The plurality of openings 16 form a pattern and contribute to the visual appearance of the film 10.

Figure 2:
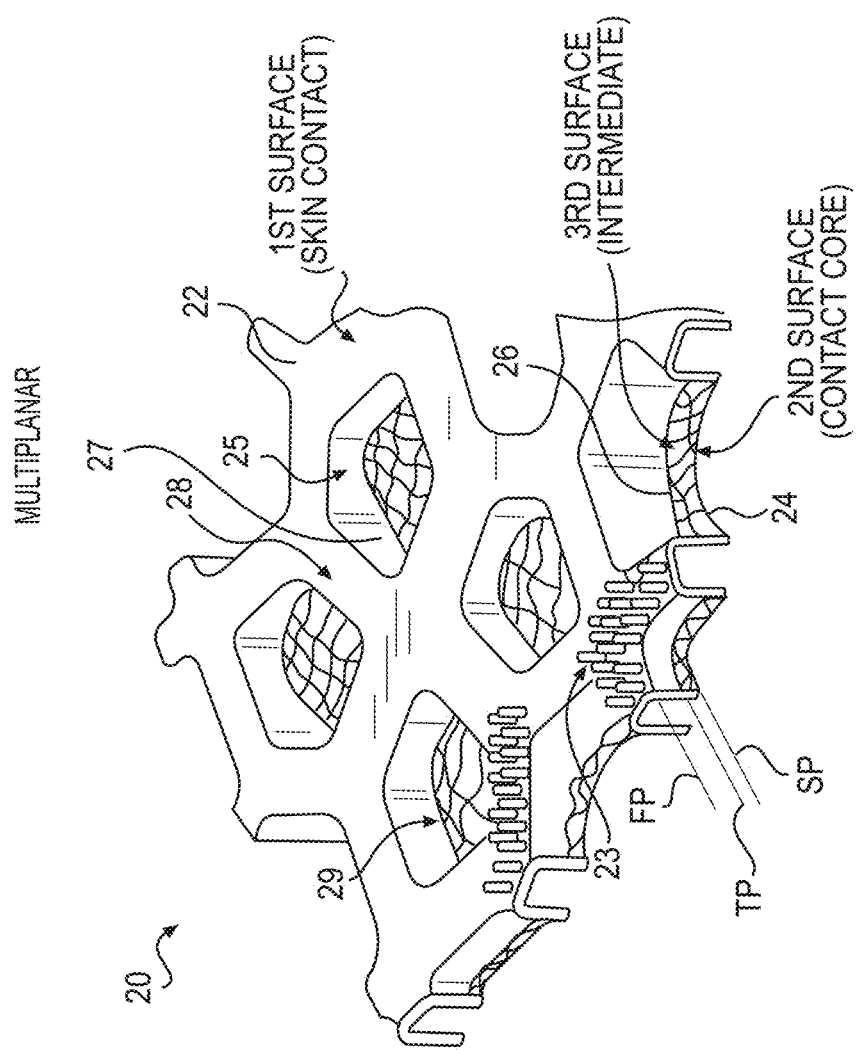
FIG. 2 is a schematic perspective view of a portion of a formed film according to an embodiment of the present invention.

FIG. 2 is a schematic perspective view of a portion of a formed film 20 according to an embodiment of the present invention. As illustrated, the film 20 is a multi-planar film that generally includes a first surface 22 generally located in a first plane FP and a second surface 24 generally located in a second plane SP. The first plane FP is spaced from and generally parallel to the second plane SP. In the illustrated embodiment, the first plane FP is located above the second plane SP. The first surface 22 may be at skin level and contact the skin of a user of an end-product, such as an absorbent article, that includes the formed film 20 when the end-product is worn by the user, and the second surface 24 will contact a core of the end-product, such as a feminine hygiene napkin.

Prior to the formation of the multi-planar structure illustrated in FIG. 2, a plurality of apertures 23 may be formed in the film via a thermoforming process, examples of which are described in further detail below. The plurality of apertures 23 may be micro-apertures arranged in a 40 to 120 mesh pattern. "Mesh" or "mesh pattern" as used herein is defined as the number of apertures or openings per linear inch. In an embodiment, the micro-apertures may be arranged in a 40 mesh pattern. In an embodiment, the micro-apertures may be arranged in a 43 mesh pattern. In an embodiment, the micro-apertures may be arranged in an 80 mesh pattern. In an embodiment, the micro-apertures may be arranged in a 100 mesh pattern. In the illustrated embodiment, each of the micro-apertures is located at the end of a three-dimensional protrusion having a male side oriented upward towards the user and configured to contact the skin of the user.

A thermoforming process may also be used to generate a plurality of openings 25 that extend from the first surface 22 to an intermediate surface 26 generally located in a third plane TP that is between the first surface 22 and the second surface 24 at the same time or subsequent to the formation of the micro-apertures 23. The formation of the plurality of openings 25 creates a plurality of "pockets," which function as gathering volumes for gathering fluids, with each pocket being circumferentially surrounded by a contiguous sidewall 27 that is part of a raised area in the form of a ridge 28. During the formation of the openings 25, ridges 28 and pockets, the portion of the film that is displaced from what remains of the first surface 22, i.e. tops of the ridges 28, may be distorted to form a porous structure, which in this embodiment is a fibrillated structure 29 that extends between the intermediate surface 26 and the second surface 24. The gathering volumes or pockets are each generally defined by the sidewalls 27, the fibrillated structure 29, and the first plane FP. The openings 25 may have any shape and the depth of the pockets may be controlled by the size of the openings 25. The illustrated embodiment is not intended to be limiting in any way.

For example, in accordance with embodiments of the invention, the first surface 22 may be designed to include raised areas that are lines or areas of any shape, e.g. geometric patterns, flowers, etc. The portion of the film generally located between the intermediate surface 26 and the second surface 24, i.e. the porous structure, may have the fibrillated structure 29, as illustrated, or may include a plurality of holes, or be void of any structure. In addition, the tops of the ridges 28 generally located in the first plane FP may or may not include the plurality of micro-apertures 23, and if the tops of the ridges 28 include a plurality of micro-apertures, the apertures may be two-dimensional apertures that have thicknesses that are approximately equal to the thickness of the original web. Also, in an embodiment (not illustrated), the protrusions may be oriented so that the male sides of the protrusions are directed towards the second plane SP.

Apparatus and Methods for Manufacturing Formed Films

Figure 3:
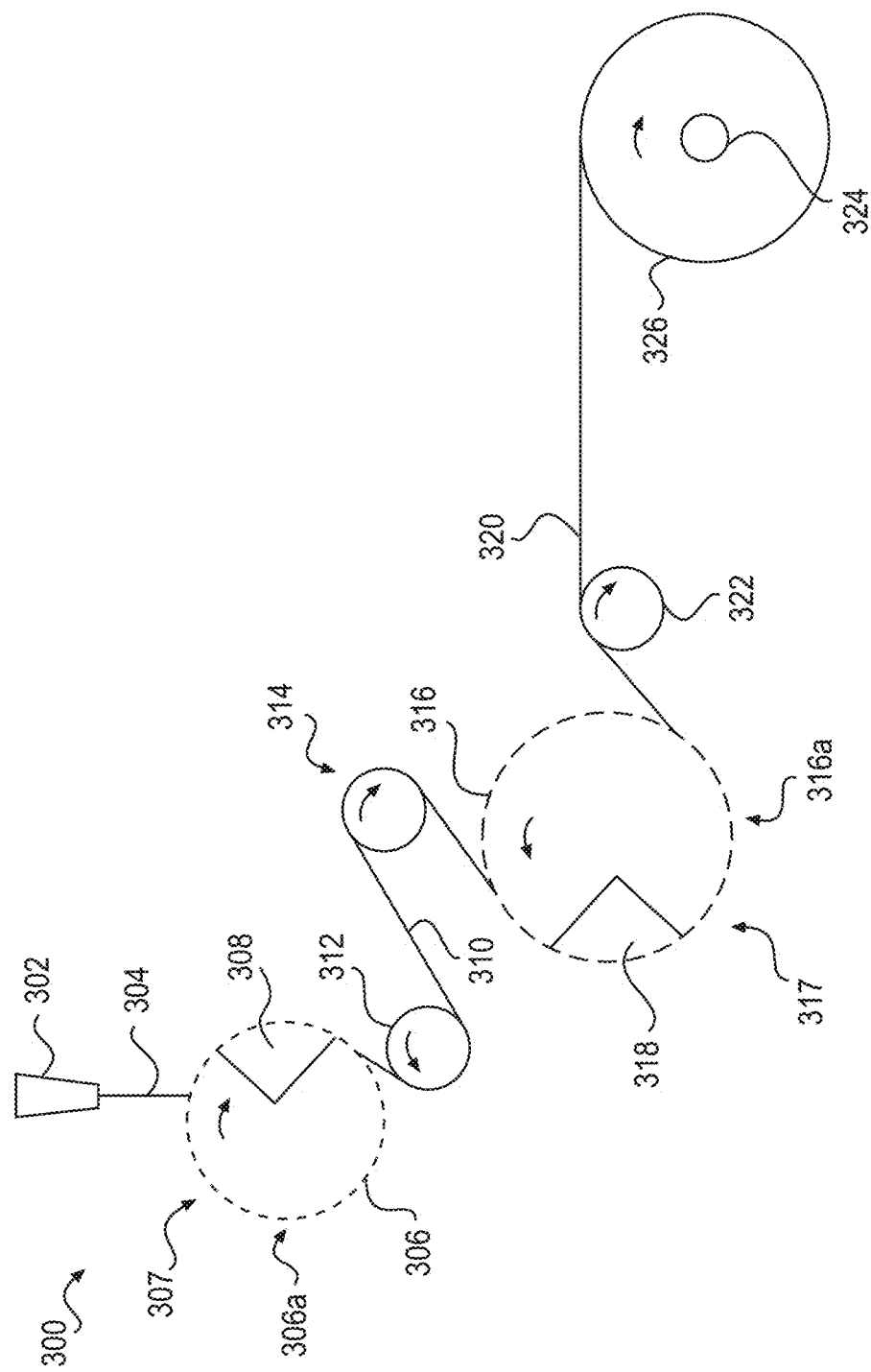
FIG. 3 is a schematic illustration of an apparatus used to form films according to embodiments of the present invention.

FIG. 3 schematically illustrates an embodiment of a vacuum forming apparatus 300 that may be used to manufacture formed films in accordance with embodiments of the invention. As illustrated, the apparatus 300 includes an extrusion die 302 that is located at the end of an extruder (not shown) and configured to form a polymer web 304 or extrudate. The polymer web 304 may be a single layer or a multi-layer polymer web, as would be understood by one of ordinary skill in the art.

In the embodiment illustrated in FIG. 3, the polymer web 304 exits the extrusion die 302 and is deposited onto a first forming structure 306 that rotates around a fixed vacuum slot 308 in which a vacuum is pulled. The first forming structure 306 and the fixed vacuum slot 308 are part of a first forming station 307. The first forming structure 306 includes a plurality of openings 306a arranged in one or more patterns. When the polymer web 304 on the first forming structure 306 passes over the vacuum slot 308, the portions of the polymer web 304 that are directly over the openings 306a in the first forming structure 306 are pulled into the openings to form protrusions on the surface of the polymer web 304 facing the first forming structure 306, and if the vacuum being pulled is high enough (more negative), apertures are formed at the end of the protrusions to form an apertured web 310. The apertured web 310 is pulled off of the first forming structure 306 by a roller 312, and travels to another roller 314 before being conveyed to a second forming structure 316 that is part of a second forming station 317. The arrangement of the two rollers 312, 314 allows the apertured web 310 to be inverted so that the surface of the web that was in contact with the first forming structure 306 does not contact the second forming structure 316.

The second forming structure 316 includes a plurality of openings 316a that are arranged in one or more different patterns than the plurality of openings 306a in the first forming structure 306. As the apertured web 310 on the second forming structure 316 passes over a fixed vacuum slot 318 in which a vacuum is pulled, portions of the apertured web 310 are pulled into the plurality of openings 316a to create a formed film 320 having a three-dimensional structure in accordance with embodiments of the invention described herein. The formed film 320 may be conveyed by one or more rollers 322 to a winder 324 and wound into a roll 326 for later conversion into an absorbent article. Additional rollers may be used throughout the apparatus 300 to convey the polymer web to the winder 324. The illustrated embodiment is not intended to be limiting in any way. For example, in another embodiment, instead of extruding the polymer web 304 directly onto the first forming structure 306, a polymer web that had been previously extruded onto a chilled roll and quenched into a solid polymer web may be reheated and conveyed to the first forming station 307.

Figure 4:
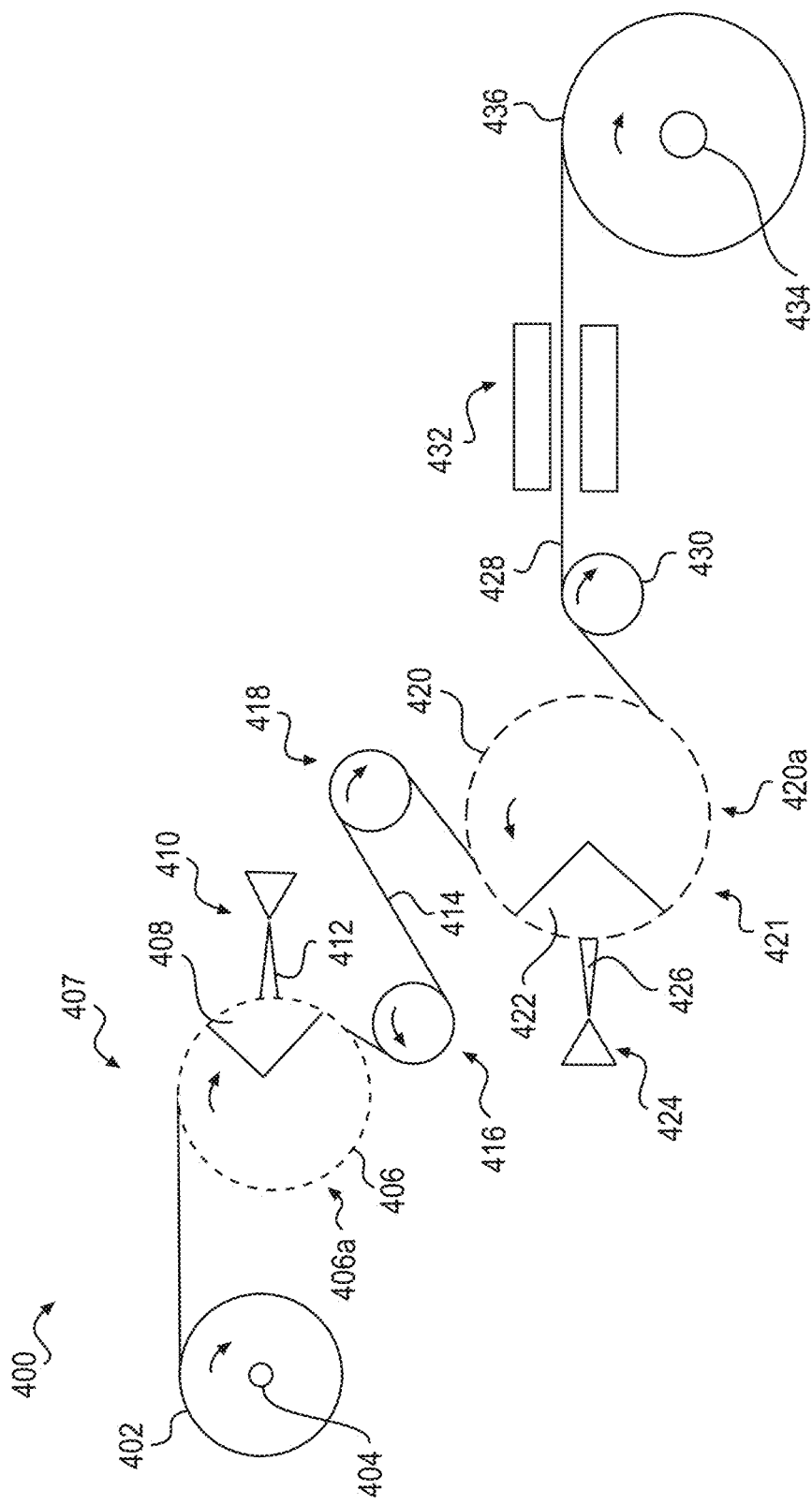
FIG. 4 is a schematic illustration of an apparatus used to form films according to embodiments of the present invention.

FIG. 4 illustrates an embodiment of a hydro-forming apparatus 400 that may be used to manufacture formed films in accordance with embodiments of the invention. As illustrated, a polymer web 402, which had been previously extruded and quenched may be unwound from a spindle 404 and conveyed to a first forming station 407 that includes a first forming structure 406 configured to rotate around a fixed vacuum slot 408. The first forming station 407 also includes a plurality of pressurized liquid jets 410 arranged in a long and narrow-width zone that extends into the paper containing FIG. 4, and is generally aligned with the fixed vacuum slot 408 under the forming structure 406. The liquid jets 410 are configured to provide overlapping streams of a liquid 412, such as water, at a pressure of from about 200 psi to about 800 psi onto an outer surface of the polymer web 402 while the web 402 is passing over the vacuum slot 408. In an embodiment, the liquid in the liquid jets 410 may have a pressure of from about 400 psi to about 800 psi. The liquid may be heated to help soften the polymer web 402. The streams of liquid 412 have sufficient pressure to push portions of the polymer web 402 into a plurality of openings 406a of the first forming structure 406 to form a plurality of protrusions having the same pattern as the plurality of openings 406a in the first forming structure 406. In an embodiment, the pressure is great enough to formed apertures at the end of the protrusions to form an apertured web 414. The vacuum being pulled in the vacuum slot 408 helps pull the liquid through the polymer web 402.

The apertured web 414 is pulled off of the first forming structure 406 by a roller 416, and travels to another roller 418 before being conveyed to a second forming structure 420 that is part of a second forming station 421. The arrangement of the two rollers 416, 418 allows the apertured web 414 to be inverted so that the surface of the web that was in contact with the first forming structure 406 does not contact the second forming structure 420.

The second forming structure 420 includes a plurality of openings 420a that are arranged in one or more different patterns than the plurality of openings 406a in the first forming structure 406. The second forming station 421 also includes a plurality of pressurized liquid jets 424 arranged in a long and narrow-width zone that extends into the paper containing FIG. 4, and is generally aligned with a fixed vacuum slot 422 under the forming structure 420. The liquid jets 424 are configured to provide overlapping streams of a liquid 426, such as water, at a pressure of from about 200 psi to about 800 psi onto an outer surface of the apertured web 414 while the web 414 is passing over the fixed vacuum slot 422. In an embodiment, the liquid in the liquid jets 424 may have a pressure of from about 400 psi to about 800 psi. The liquid may be heated to help soften the apertured web 414. The streams of liquid 426 have sufficient pressure to push portions of the apertured web 414 into the openings of the second forming structure 420.

As the apertured web 414 on the second forming structure 420 passes over the fixed vacuum slot 422 in which a vacuum is pulled, portions of the apertured web 414 are pulled into the plurality of openings to create a formed film 428 having a three-dimensional structure in accordance with embodiments of the invention described herein. The formed film 428 may be conveyed by one or more rollers 430 to a dryer 432 so that any residual liquid from the jets 410, 424 may be removed from the formed film 428 before being conveyed to a winder 434 and wound into a roll 436. Additional rollers may be used throughout the apparatus 400 to convey the polymer web to the winder 434. The illustrated embodiment is not intended to be limiting in any way. For example, in another embodiment, instead of unwinding the polymer web 402 from the spindle 404, the quenched polymer web may be conveyed directly from the chill roll after exiting an extrusion die to the first forming station 407. In other words, aspects of the apparatus 300 illustrated in FIG. 3 may be provided in the apparatus 400 illustrated in FIG. 4, and vice-versa.

The forming structures of the apparatus 300, 400 described above may include various meshes (openings per linear inch) and designs that may be used to create the micro-apertures, the porous structures, and the raised areas described herein. For example, a forming structure having a mesh pattern between 40 and 120 mesh, such as 80 mesh or 100 mesh, may be used in the first forming station to form micro-apertures in the polymer web. Then, a forming structure having a 40 mesh or 43 mesh pattern may be used as an underlying forming structure and a second forming structure having a skeleton-like structure having solid areas in the form of lines (straight and/or curved) or, for example, in the shape of flower petals, and large openings in between the solid areas may be placed on top of the underlying forming structure in the second forming station. In an embodiment, the underlying forming structure and skeleton-like structure may be integrated as one forming structure for the second forming station. The solid areas in the skeleton-like structure form the raised areas and the large openings form the gathering volumes in the formed films described herein. A combination of the micro-apertures already formed in the polymer web, the openings in the underlying forming structure, and the skeleton-like structure create the porous structures at the bottoms of the gathering volumes. It should be appreciated by those of ordinary skill in the art that the embodiments of the formed film described herein will have associated forming structure designs that may be used in the apparatus 300, 400 described above.

If a forming structure having a 43 mesh pattern is to be used in the hydro-forming apparatus 400 of FIG. 4, the design described by U.S. patent application Ser. No. 15/374,567, filed Dec. 9, 2016, which is incorporated by reference in its entirety, may be used. As described therein, the forming structure may have a 55.5 mesh pattern in the machine direction (i.e. the direction of rotation of the forming structure), and a 43.5 mesh pattern in the transverse direction that is perpendicular to the machine direction. Such a pattern may still be referred to as a 43 mesh pattern.

The forming structures may have uniform patterns or may have different zones containing different patterns or no patterns. For example, different zones may have different mesh patterns that will be transferred to the polymer web.

Example 1

A three-layer web having a middle (core) layer and two outer (skin) layers was coextruded through an extrusion film die having a set temperature of about 500° F. The core layer was about 71.4% of the overall film thickness and each of the skin layers was about 14.3% of the overall film thickness. The core layer was a blend consisting essentially of about 46 wt % linear low density polyethylene (LLDPE), about 34 wt % high density polyethylene (HDPE), about 12 wt % polyethylene-based masterbatch comprising a surfactant, and about 8% polyethylene-based masterbatch comprising a white pigment. Each of the skin layers was a blend consisting essentially of about 42 wt % LLDPE, about 42 wt % HDPE, and about 16 wt % low density polyethylene (LDPE). The three-layer extrudate exited the die and was cast onto a casting roll with a rotational speed set so that the web advanced about 250 feet/minute.

A first forming structure having a plurality of holes arranged in an 80 mesh pattern was used to create a plurality of micro-apertures in the web. A second forming structure was used to create a plurality of openings that formed a plurality of pockets having fibrillated structures at the bottoms of the pockets. The second forming structure comprised an inner part having a plurality of oval-shaped openings arranged in in a 40 mesh pattern, with major axes of the openings oriented in a direction transverse to the machine direction of the web, and a second part placed on top of the first part having a design of a plurality of interconnected raised lines. The resulting film is illustrated in FIGS. 5A and 5B.

Figure 5B:
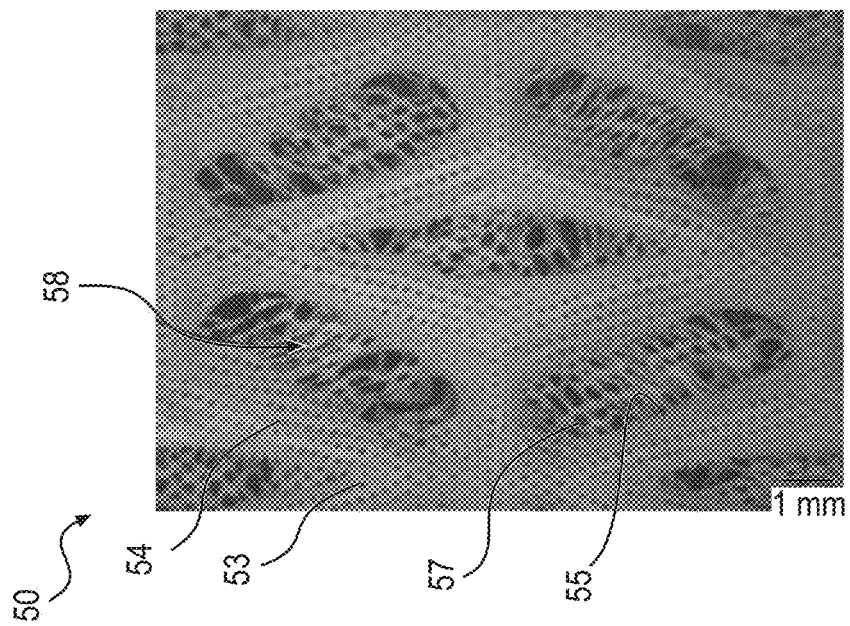
FIG. 5B is a more detailed top view of a portion of the formed film illustrated in FIG. 5A.
Figure 5A:
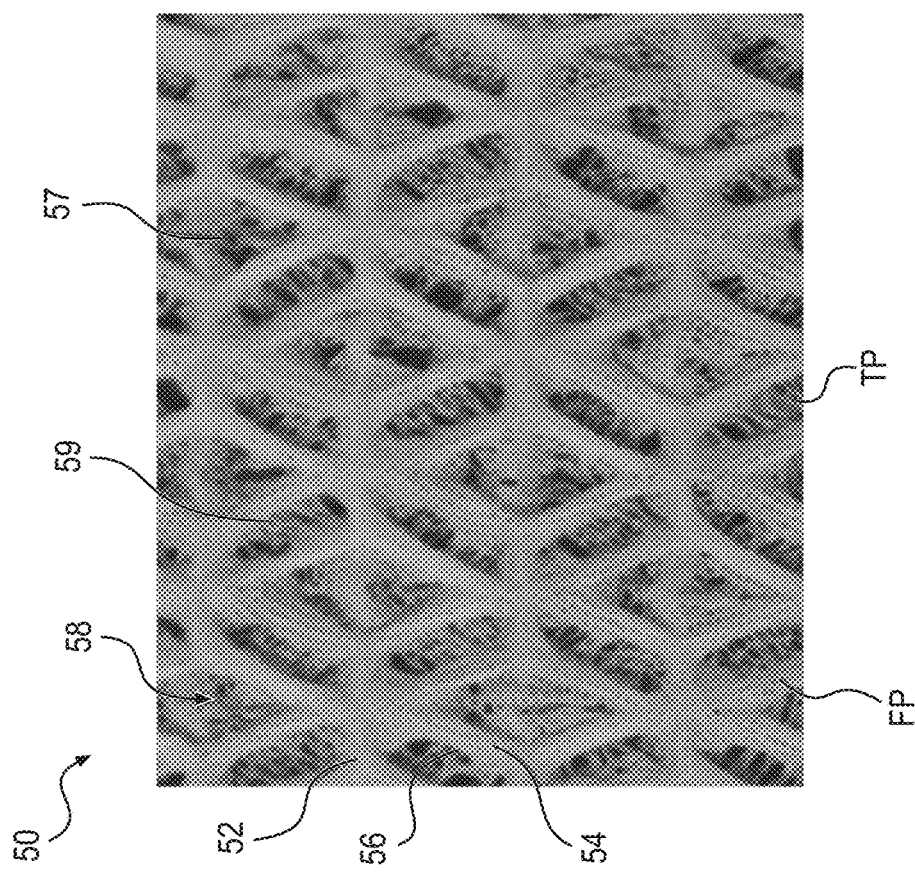
FIG. 5A is a top view of a portion of a formed film according to an embodiment of the present invention.

FIG. 5A is a top view of a portion of a formed film 50 according to an embodiment of the present invention, and FIG. 5B is a more detailed top view of a portion of the formed film 50 illustrated in FIG. 5A. As illustrated, the film 50 includes a first surface 52 generally located in a first plane FP and a second surface generally located in a second plane that is spaced from the first surface 52 at a depth running into the paper. The film 50 includes a plurality of raised areas in the form of ridges 54 having tops and sidewalls that are connected and extend from the first surface 52 to an intermediate surface 56 that is generally located in a third plane TP, in between the first plane FP and the second plane, such that tops of the ridges 54 generally lie in the first plane FP. Openings 58 between the tops of the ridges 54 create "gathering volumes" or "pockets" or "gathering channels" that are defined on one end by the intermediate surface 56 and on an opposite end by the first plane FP, and surrounded by sidewalls 55 of the ridges 54. A porous or fibrillated structure 59 of the film 50 generally extends between the intermediate surface 56 and the second surface. The fibrillated structure 59 has a plurality of openings 57 that have non-uniform, random, and irregular shapes as created during formation of the fibrillated structure 59 at the second forming station described above. In the embodiment illustrated in FIGS. 5A and 5B, all of the surfaces of the film 50 that are not part of the fibrillated structure 59, i.e. the tops and sidewalls of the ridges 54, include micro-apertures 53 that are generally circular or slightly elliptical in shape. The micro-apertures 53 may be at the ends of protrusions having male and female ends, with the male ends on the tops of the ridges 54 generally located at the first surface 52. The micro-apertures 53 were formed at the first forming station described above. The illustrated embodiment is not intended to be limiting in any way.

Figure 6B:
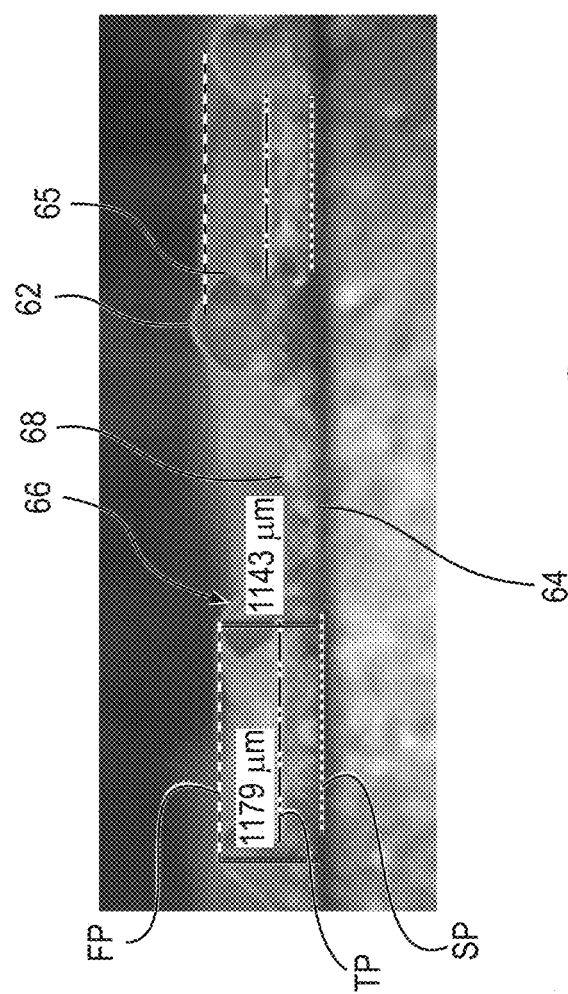
FIG. 6B is a cross-sectional view of the formed film of FIG. 6A generally taken along line 6B-6B in FIG. 6A.
Figure 6A:
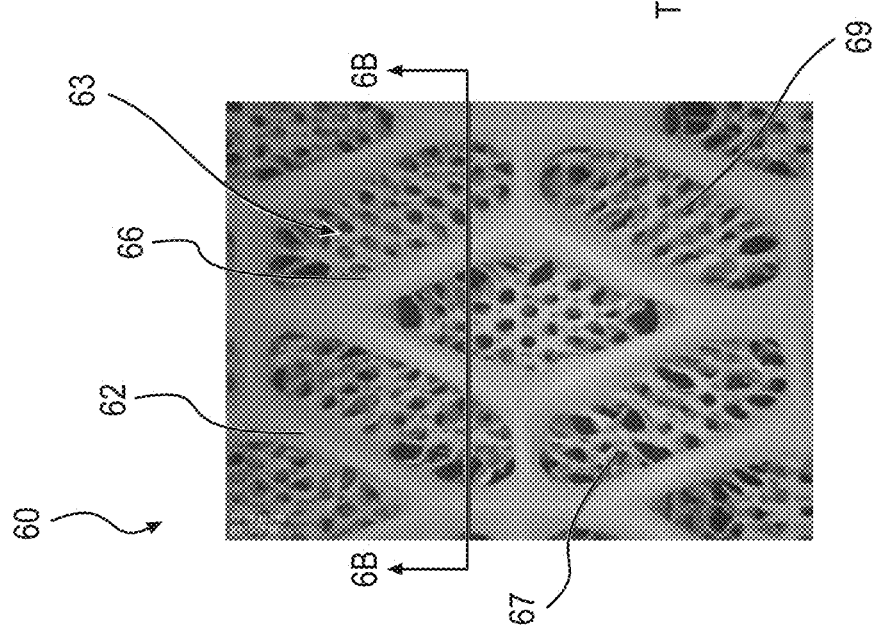
FIG. 6A is a top view of a portion of a formed film according to an embodiment of the present invention.

For example, the film may not include the micro-apertures 53 that are illustrated in FIGS. 5A and 5B. FIG. 6A is a top view of a portion of a formed film 60 according to an embodiment of the present invention, and FIG. 6B is a cross-sectional view generally taken along line 6B-6B in FIG. 6A. The film 60 includes a first surface 62 generally located in a first plane FP, and a second surface 64 generally located in a second plane SP that is spaced from the first plane FP at a depth running into the paper in FIG. 6A, as illustrated in FIG. 6B. The film 60 includes a plurality of openings 63 circumferentially surrounded by plurality of raised areas or ridges 66 that include tops that form the first surface 62 and have sidewalls 65 that extend from the first plane FP to a third surface 68 generally located in a third plane TP in between the first plane FP and the second plane SP. As illustrated in FIG. 6B, the distance between the first plane FP and the second plane SP (i.e. the caliper or embossed thickness) is about 1200 μm. A porous or fibrillated structure 69 of the film 60 generally lies in between the second plane SP and the third plane TP and generally defines the second surface 64 and the third surface 68. The fibrillated structure 69 has a plurality of openings 67 that have non-uniform, random, and irregular shapes as illustrated in FIG. 6A.

In the embodiments illustrated in FIGS. 6A-6B, the openings between the tops of the ridges and the fibrillated structures create "gathering volumes" or "pockets" between the sidewalls of the ridges. It has been found that the pockets may be effective in quickly removing body fluid away from the skin of the user when worn by the user, as discussed in further detail below. In addition, the fibrillated structures 59, 69 of the films 50, 60 may prevent rewet and assure relatively good conversion when incorporated into the absorbent article end-product.

Example 2

A coextruded web similar to the web described above in Example 1 was used to create a formed film 70 in accordance with an embodiment of the invention. After the web exited the extrusion die and was cast on a casting roll, a first forming structure having a plurality of holes arranged in a 43 mesh pattern was used to create a plurality of micro-apertures in the web. A second forming structure having a plurality of grooves with spaced apart openings at the bottoms of the grooves was used to create a formed film having a plurality of openings at a lower surface and a plurality of raised areas at an upper surface of the formed film.

Figure 7:
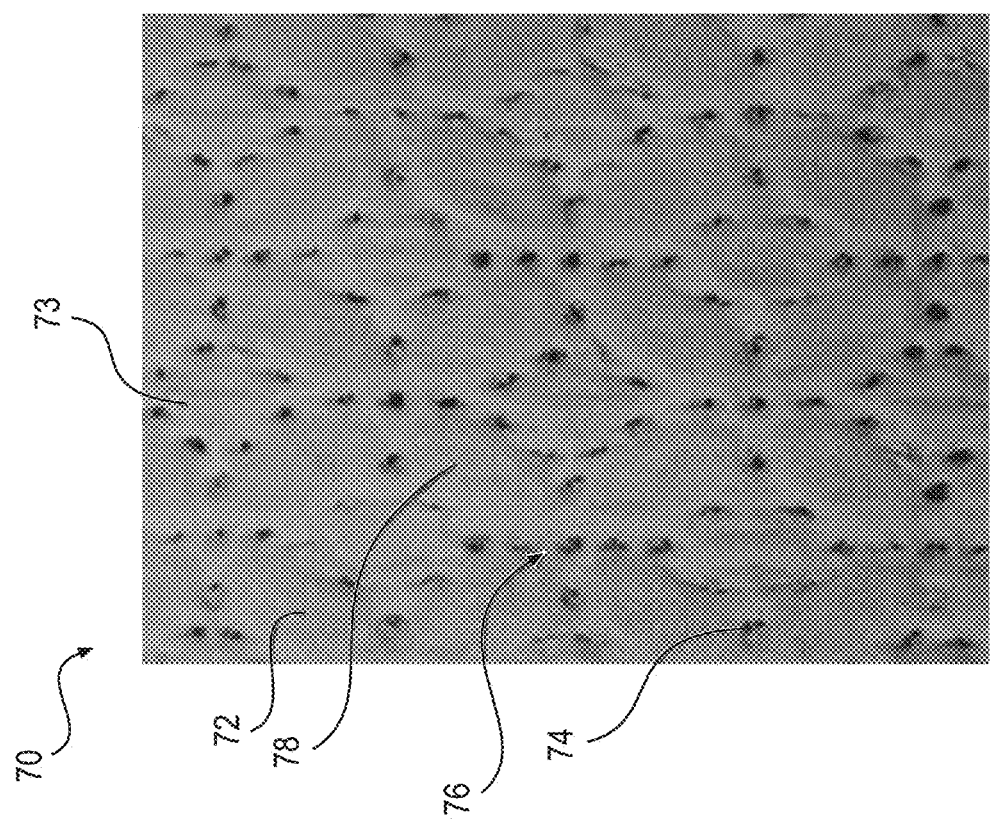
FIG. 7 is a top view of a portion of a formed film according to an embodiment of the present invention.

As illustrated in FIG. 7, the film 70 includes a plurality of micro-apertures 72, and a plurality of macro-apertures 74 along grooves 76 relative to a top surface 73 of the film 70. The grooves 76 and the macro-apertures 74 define raised areas 78 that are arranged in a flower-like pattern. The raised areas 78 that are defined by the macro-apertures 74 and the grooves 76 are raised relative to the macro-apertures 74 such that the tops of the raised areas 78 generally lie in a first plane and create a skin level surface that contacts the user when worn by the user. The macro-apertures 74 terminate in a second plane that is spaced from the first plane in a direction into the page such that successive macro-apertures 74 help define the grooves 76 in the film.

Figure 8:
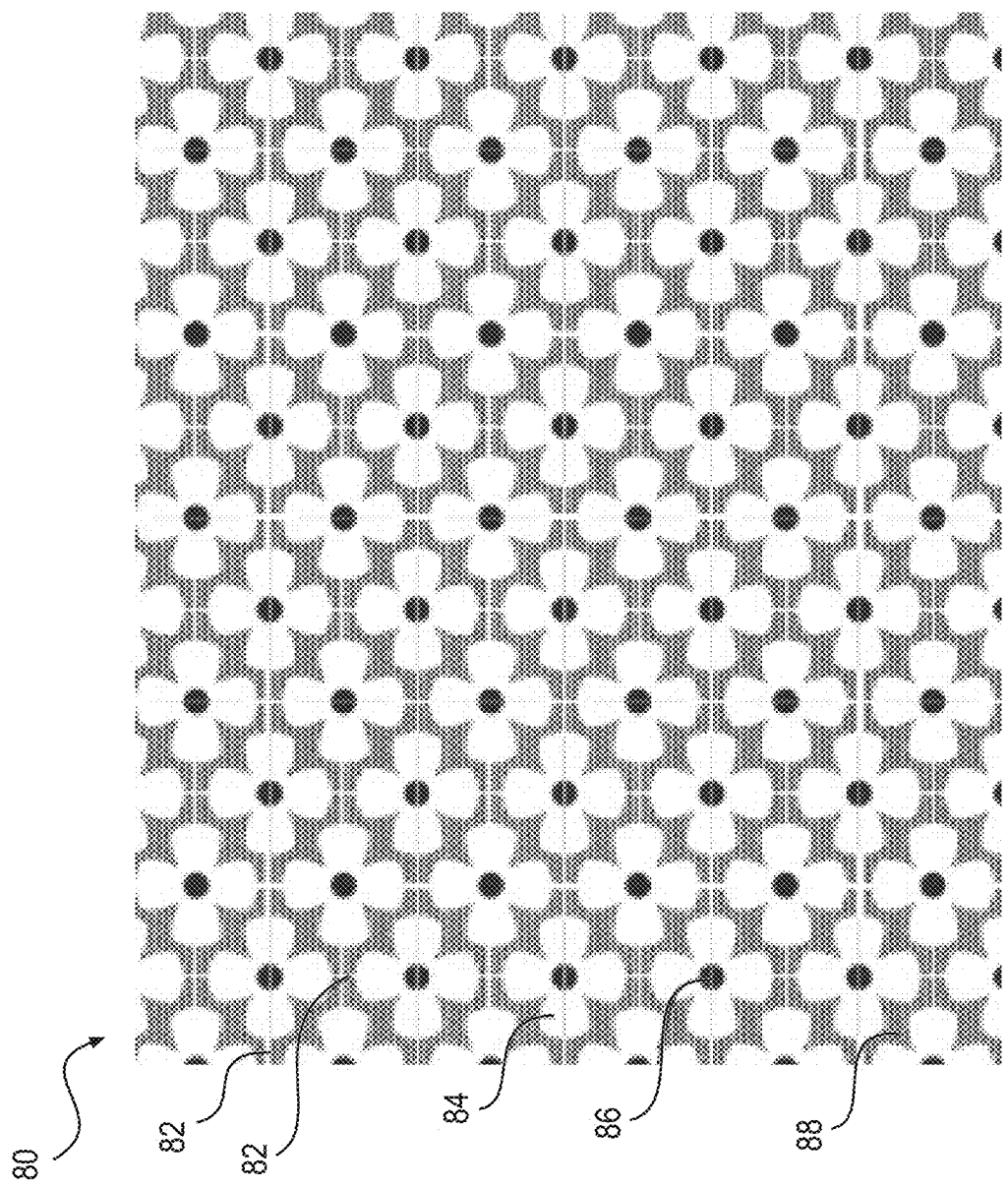
FIG. 8 is a schematic view of a portion of a formed film according to embodiments of the invention.

FIG. 8 is a schematic view of a portion of a formed film 80 according to embodiments of the invention that illustrates the concept that endless designs may be engineered by combining four different features of the formed films represented by the films 20, 50, 60, 70 illustrated in FIGS. 2 and 5-7, and described above. For example, the film 80 may include features in the form of raised lines or ridges 82 (represented by white lines in FIG. 8), raised areas 84 (which look like flowers in FIG. 8), macro-apertures or holes 86 (represented by the black circles in FIG. 8), and porous or fibrillated structures 88 (represented by the grey areas in FIG. 8). The various features 82, 84, 86, 88 may be combined in different patterns. As demonstrated by the formed films illustrated in FIGS. 2 and 5-7, not all of the features 82, 84, 86, 88 need to be present in the same film, and other combinations not illustrated are contemplated as being part of the scope of the present invention. The features 82, 84, 86, 88 may be imparted to the film 80 by using suitable forming structures and methods for using such structures in a manufacturing process, as understood by one of ordinary skill in the art.

Example 3

Figure 9B:
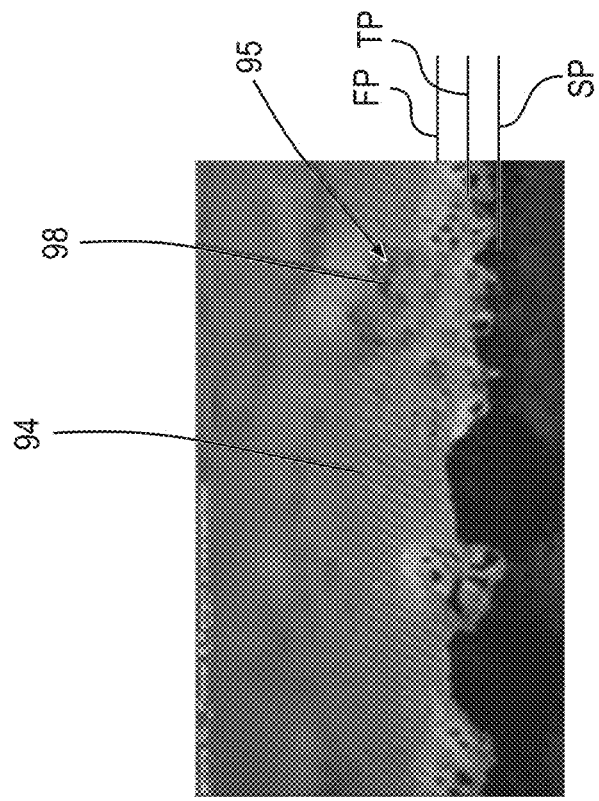
FIG. 9B is a cross-sectional view of the formed film of FIG. 9A generally taken along line 9B-9B in FIG. 9A.
Figure 9A:
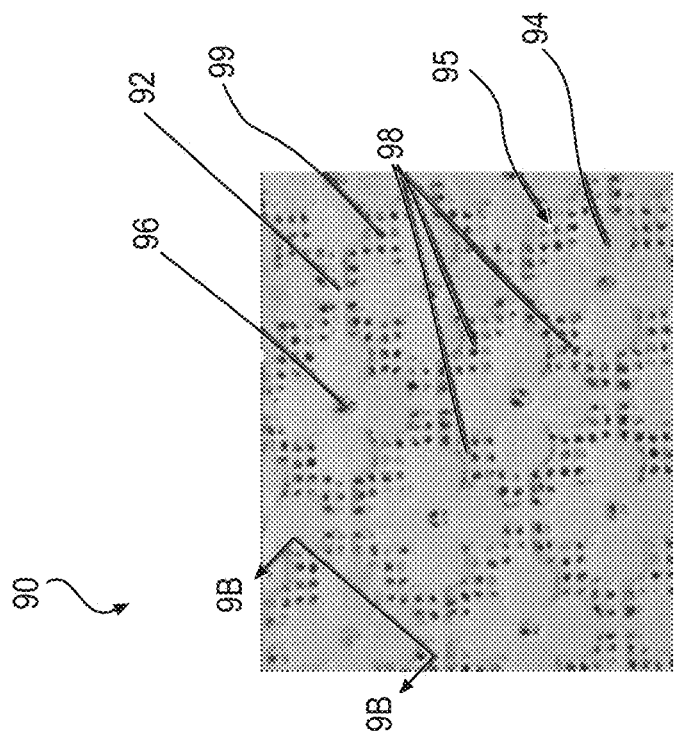
FIG. 9A is a top view of a portion of a formed film according to an embodiment of the present invention.

FIG. 9A illustrates an embodiment of a formed film 90 that contains the design schematically illustrated in FIG. 8, and FIG. 9B is a cross-sectional view of the formed film 90 generally taken along line 9B-9B in FIG. 9A. The formed film 90 includes raised lines or ridges 92 that connect raised areas or lands 94 that are shaped like petals of a flower, macro-apertures or holes 96 in the center of each raised area 94, and a porous or fibrillated structure or net 98. Tops of the raised lines 92 and raised areas 94 generally define a top surface of the formed film 90 and are generally located in a first plane FP, and the porous or fibrillated structure 98 extends between a second plane SP, in which a bottom surface of the film generally lies, and a third plane TP that is in between the first plane FP and the second plane SP. When the formed film 90 is used as a topsheet of an absorbent article that is worn by a user, the top surface formed by the raised areas 94 and lines 92 is in contact with the user's skin and the bottom surface is in contact with an absorbent core of the article. The raised areas 94 provide relatively wide, "puffy" areas that may provide a silky softness to the user. A plurality of pockets or gathering channels (volumes) 95 are defined by sidewalls of the raised lines 92, the first plane FP and the porous or fibrillated structure 98. In the illustrated embodiment, the porous or fibrillated structure 98 is a net-like structure that includes a plurality of apertures 99 having a generally square shape.

In order to investigate the effect of the area of the porous or fibrillated structure 98 between the raised lines 92 and raised areas 94 of the formed film and resulting volume of the gathering volumes or channels 95 on fluid handling performance, a plurality of samples having different spacing between the raised areas 94 were created. By increasing the spacing between the raised areas 94, the area of the porous or fibrillated structure 98 between the raised areas 94 was increased, which increased the volume of the gathering channels (volumes) 95. The lengths of the raised lines 92 were also increased. In one embodiment, the area of the raised areas was decreased and the area of the fibrillated structure and volume of the gathering channels was increased. FIGS. 10A, 10B, 10C and 10D illustrate the samples that were created.

Table I lists the areas (in square inches and percentages of total area) of the porous or fibrillated structures 108, raised land areas 104, holes 106 and raised lines 102 of formed films 100A, 100B, and 100C illustrated in FIGS. 10A, 10B, and 10C, respectively. The raised lines 92 were used in the designs to improve processing of the film and to provide strength to the forming structure that was used to form the raised areas 94 and lines 92. The holes 96 were added to provide more appealing visual appearance.

TABLE I

Areas of Portions of Formed Films

| Formed Film Sample in FIGS. 10A-10C | Porous/Fibrillated Structure 108 | Raised Areas 104 | Holes 106 | Raised Lines 102 |
|---|---|---|---|---|
| 100A | 0.153 in$^2$ | 0.232 in$^2$ | 0.013 in$^2$ | 0.007 in$^2$ |
| 100A | 37.9% | 57.2% | 3.1% | 1.8% |
| 100B | 0.231 in$^2$ | 0.232 in$^2$ | 0.013 in$^2$ | 0.011 in$^2$ |
| 100B | 47.4% | 47.6% | 2.6% | 2.4% |
| 100C | 0.308 in$^2$ | 0.232 in$^2$ | 0.013 in$^2$ | 0.016 in$^2$ |
| 100C | 54.2% | 40.8% | 2.2% | 2.8% |

Formed films 100A, 100B and 100C had the same raised (land) areas and hole areas, but different porous/fibrillated structure areas and raised line areas. As illustrated in FIG. 10D, formed film 100D had decreased raised (land) areas and increased porous/fibrillated structure areas, as compared to formed films 100A, 100B and 100C.

Returning to FIGS. 9A and 9B, because the porous/fibrillated structure 98 and therefore gathering channels/volumes 95 surround the raised (land) areas 94 and the fibrillated structure 98 is lower than the top surface of the raised areas 94 that is generally in the first plane FP, the gathering channels/volumes 95 may be helpful in collecting (i.e. gathering) fluids and transferring the fluids into the absorbent core of the absorbent article that will be located below the porous/fibrillated structure 98 in use. Also, because the gathering channels/volumes 95 interrupt the continuous raised land surface 94 (with the small exception of the solid lines 92), the gathering channels 95 may be helpful in blocking the distribution of the fluids on the land areas 94 and fostering the transfer of the fluids into the core of the absorbent article. The body fluids may find obstacles in transferring onto the raised land area (top surface) 94 and therefore may collect in the gathering channel areas 95 and quickly move away from the user's skin. From the gathering channel 95, the fluid may be transferred into the core through openings 99 of the porous/fibrillated structure 98. The amount of area in direct contact with the user's skin may be reduced because the gathering channel 95 is lower than the top surface of the formed film 90. The formed film 90 was used as Example 3 in the testing discussed below.

Example 4

Figure 11:
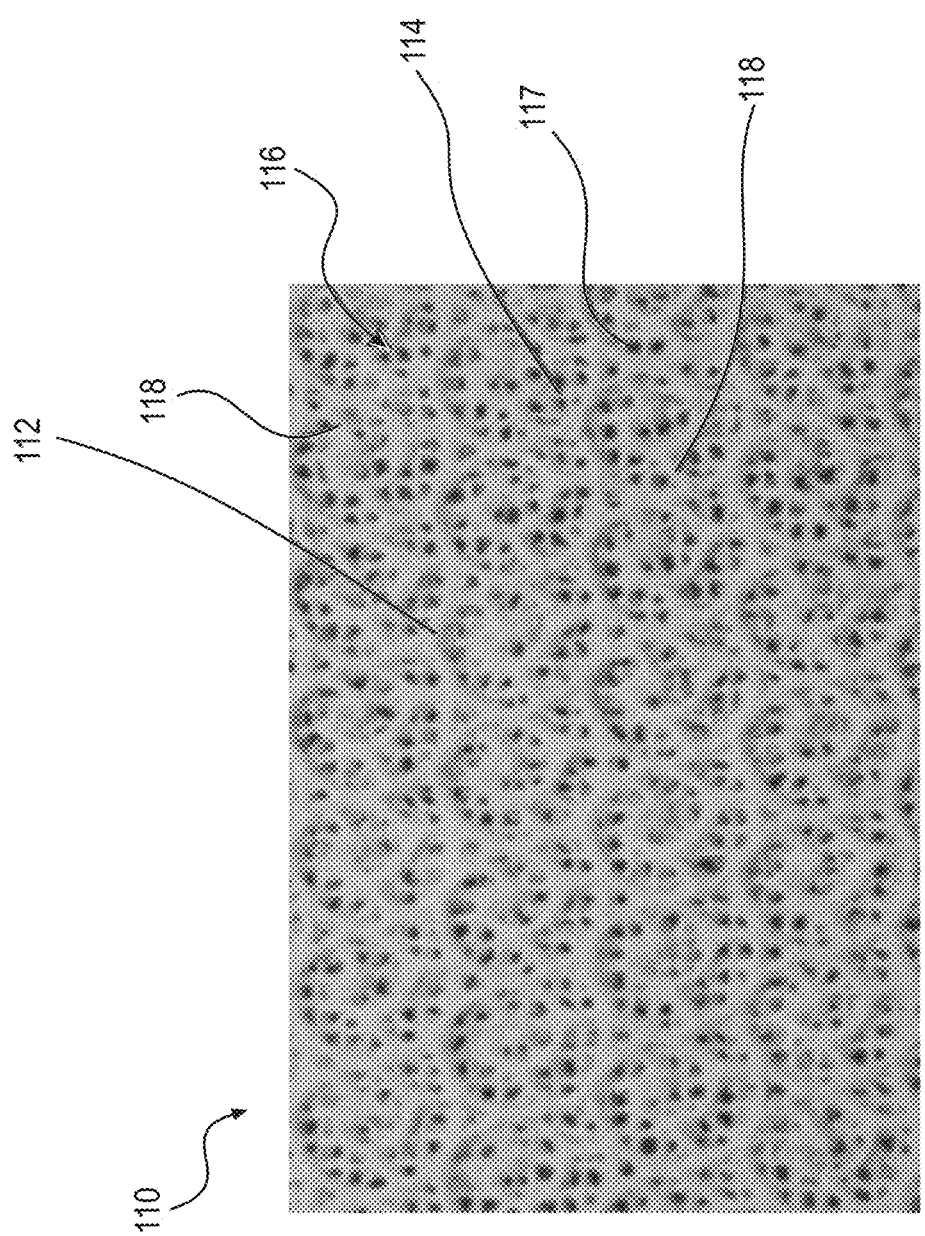
FIG. 11 is a top view of a portion of a formed film according to an embodiment of the present invention.

FIG. 11 illustrates an embodiment of a formed film 110 that includes raised land areas in the form of curved raised lines 112 that form the shape of a shell. A fibrillated or porous structure 114 is recessed from a top surface of the curved raised lines 112 and the curved raised lines 112 and the fibrillated/porous structure 114 together define curved gathering channels (i.e. gathering volumes) 116 having openings 117 through a bottom surface thereof (i.e. through the fibrillated structure 114). Additional raised lines 118 that are generally straight and span across the curved gathering channels 116 may be used to strengthen the overall structure of the formed film 110. As illustrated, the depressed gathering channels 116 are relatively large as compared to the land areas 112. During the insult of body fluids, the fluid may be quickly transferred into the depressed gathering channels 116 and kept away from the land areas 112, which are in contact with the user's skin when worn as part of an absorbent article by the user. Because the land areas 112 are relatively small, the amount of fluid that is spread (i.e. distributed) on the land area 112 (top surface) may be minimized. The formed film 110 was used as Example 4 in the testing discussed below.

Without being bound by theory, it is thought that due to the curved design of the raised areas, fluid that contacts the raised areas will initially travel along the raised areas for a short distance, but will be quickly drawn into the gathering channels, because the fluid will tend to move along a straight line. In other words, the fluid is less likely to stay on the curved raised area and more likely to travel along a straight line and into a gathering channel. The spiral design provides a mechanism for gathering fluids in the gathering channels more quickly than films of the prior art.

Example 5

Figure 12C:
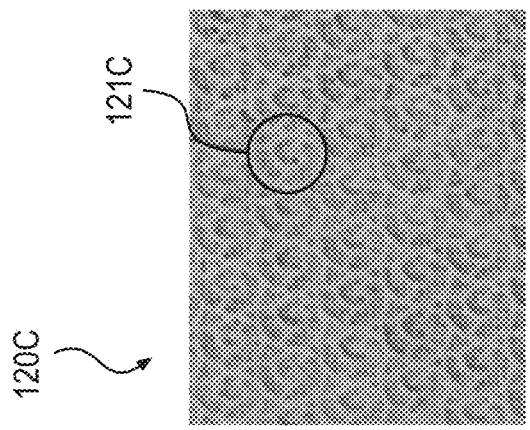
FIGS. 12A-12C are top views of portions of formed films according to embodiments of the present invention.
Figure 12B:
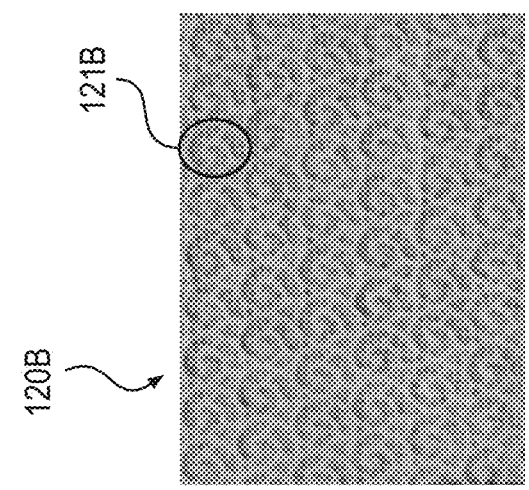
Figure 12A:
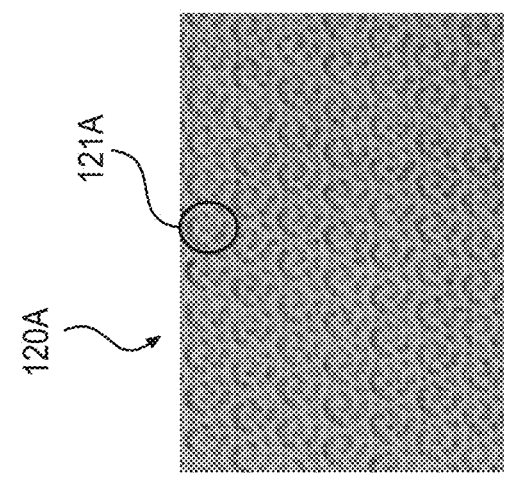

FIGS. 12A, 12B and 12C illustrate formed films 120A, 120B and 120C, respectively, according to embodiments of the present invention. The formed film 120A is generally of the same design as the formed film 110 of FIG. 11. The dimension of the "shell" 121B in the design of formed film 120B in FIG. 12B is about 25% larger than the dimensions of the "shell" 121A in the design of formed film 120A in FIG. 12A, and the dimensions of the "shell" 121C in the design of formed film 120C in FIG. 12C is about 40% larger than the dimensions of the "shell" 121A in the formed film 120A in FIG. 12A. The formed film 120B of FIG. 12B was used as Example 5 in the testing discussed below.

Figure 13:
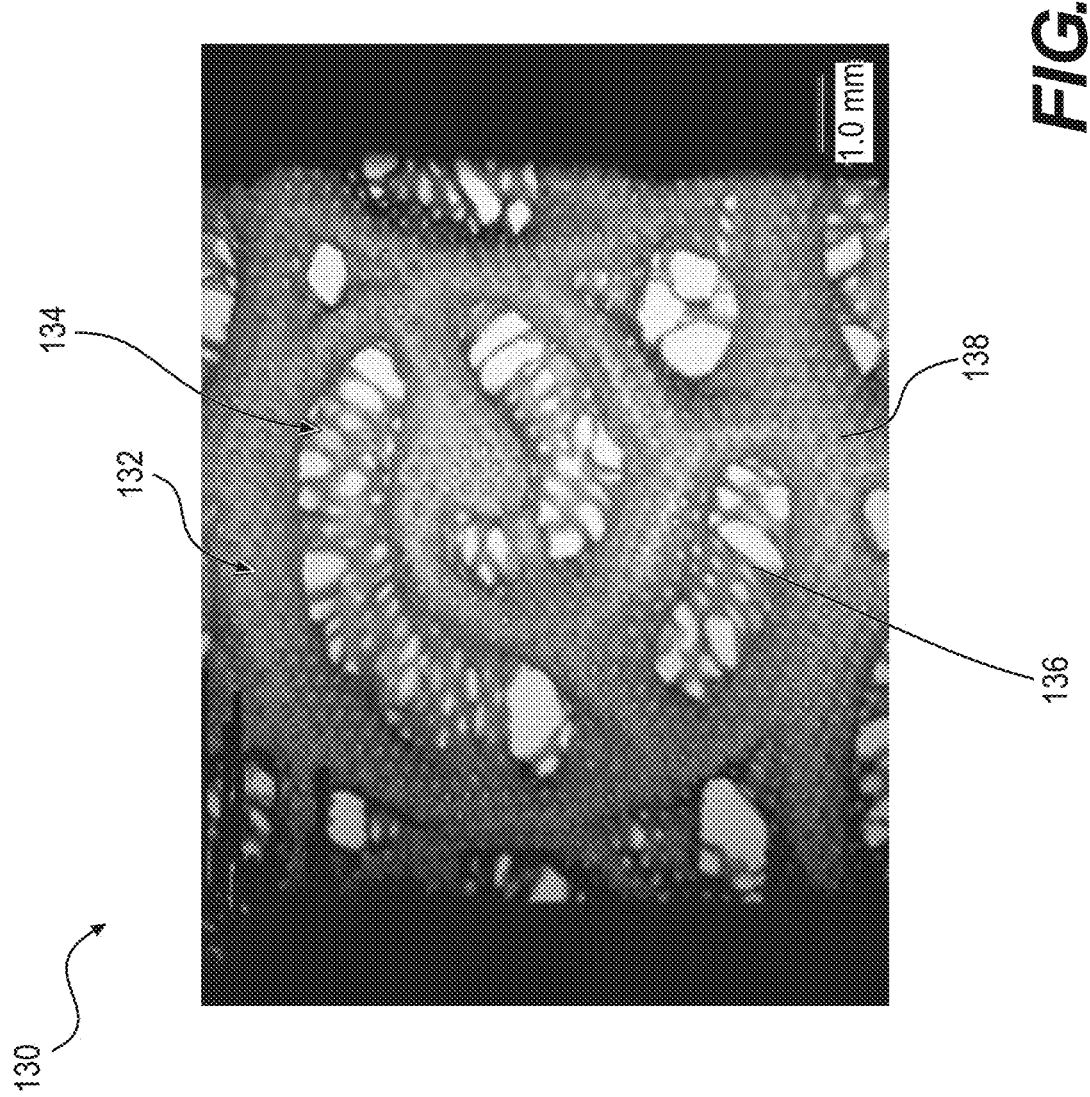
FIG. 13 is a top view of a portion of a formed film according to an embodiment of the present invention.

FIG. 13 illustrates a portion of an embodiment of a formed film 130 having the same general design as the formed film 120A of FIG. 12A. As illustrated, the formed film 130 has raised areas 132 that are shaped as a shell, and the raised areas 132 define a plurality of gathering volumes or channels 134 that have porous structures 136 spaced below the raised areas 132. The raised areas 132 having a plurality of apertured micro-protrusions 138 extending above lands of the raised areas 132. The raised areas 132 generally define the surface that will contact a user wearing an absorbent article that includes the formed film 130 as its topsheet or top layer. For the unit "shell" illustrated in FIG. 13, a skin contact area, which is the combined area of the raised areas 132 was estimated to be about 45% of the total area of the unit "shell", with the area in the gathering volumes 134 estimated to be about 55% of the total area of the unit "shell." This ratio may be altered by changing the design of the forming structure used to form the raised areas in the second forming station described above.

It is expected that when the formed films according to embodiments of the invention are wound by a winder into a roll, the formed films will compress and their calipers as well as air permeabilities will decrease from the outside of the roll to the core. In other words, portions of the formed films located toward the outside of a roll will likely have a greater caliper than portions of the formed film located towards the center of the roll. To study this effect, three different formed films having the repeating "shell" pattern generally illustrated in FIG. 12A were made using different blends of polymers. The films were wound onto paper cores having diameters of about 8 inches until the rolls of the formed films were about 39 inches in diameter. Control samples were cut from the outside layers of the rolls immediately after production, and analyzed after being aged approximately 8 to 30 days for their embossed thickness (i.e. caliper) and air permeability. The embossed thicknesses were measured following ASTM D645, but using an anvil with a diameter of 2 inches. Samples were taken from each of the three rolls at various positions from the cores, and seven measurements were taken for each sample. The embossed thickness results are listed in Table II and the air permeability results are listed in Table III below.

TABLE II

| | Embossed Thickness Results | | |
|---|---|---|---|
| Sample Position | Blend 1 Embossed Thickness (μm)/ % Decrease from Control | Blend 2 Embossed Thickness (μm)/ % Decrease from Control | Blend 3 Embossed Thickness (μm)/ % Decrease from Control |
| Control | 920.3 μm | 874.8 μm | 852.4 μm |
| 15 inches from core | 816.0 μm/88.7% | 776.1 μm/88.7% | 753.0 μm/88.3% |
| 14 inches from core | 738.0 μm/80.2% | 746.5 μm/85.3% | 736.7 μm/86.4% |
| 12 inches from core | 730.3 μm/79.4% | 693.7 μm/79.3% | 708.9 μm/83.2% |
| 10 inches from core | 695.9 μm/75.6% | 687.3 μm/78.6% | 726.4 μm/85.2% |
| 8 inches from core | 692.3 μm/75.2% | 677.4 μm/77.45 | 674.1 μm/79.1% |
| 6 inches from core | 699.1 μm/76.0% | 670.9 μm/76.7% | 643.3 μm/75.5% |
| 4 inches from core | 660.9 μm/71.8% | 656.5 μm/75.0% | 627.9 μm/73.7% |
| 2 inches from core | 647.0 μm/70.3% | 626.0 μm/71.6% | 608.3 μm/71.4% |

The results listed in Table II indicate a similar trend across all three blends; the calipers (embossed thicknesses) of the formed films tested decreased as the samples were taken from the outside of the rolls towards the cores. Overall, the calipers ranged from about 600 μm to about 920 μm, depending on where the samples were taken, as well as the specific polymer blend used to extrude the initial polymer web.

TABLE III

Air Permeability Results

| Sample Position | Blend 1 Air Permeability ($m^3/m^2/min$)/ % Decrease from Control | Blend 2 Air Permeability ($m^3/m^2/min$)/ % Decrease from Control | Blend 3 Air Permeability ($m^3/m^2/min$)/ % Decrease from Control |
|---|---|---|---|
| Control | 182.7 $m^3/m^2/min$ | 183.9 $m^3/m^2/min$ | 177.4 $m^3/m^2/min$ |
| 15 inches from core | 159.9 $m^3/m^2/min$/ 87.5% | 159.1 $m^3/m^2/min$/ 86.5% | 154.6 $m^3/m^2/min$/ 87.1% |
| 14 inches from core | 142.3 $m^3/m^2/min$/ 77.9% | 142.4 $m^3/m^2/min$/ 77.4% | 137.7 $m^3/m^2/min$/ 77.6% |
| 12 inches from core | 139.7 $m^3/m^2/min$/ 76.5% | 136.7 $m^3/m^2/min$/ 74.3% | 133.7 $m^3/m^2/min$/ 75.4% |
| 10 inches from core | 138.4 $m^3/m^2/min$/ 75.7% | 131.3 $m^3/m^2/min$/ 71.4% | 132.3 $m^3/m^2/min$/ 74.5% |
| 8 inches from core | 128.9 $m^3/m^2/min$/ 70.6% | 133.4 $m^3/m^2/min$/ 72.5% | 128.0 $m^3/m^2/min$/ 72.2% |
| 6 inches from core | 128.9 $m^3/m^2/min$/ 70.6% | 128.8 $m^3/m^2/min$/ 70.0% | 124.6 $m^3/m^2/min$/ 70.2% |
| 4 inches from core | 126.3 $m^3/m^2/min$/ 69.1% | 125.7 $m^3/m^2/min$/ 68.4% | 122.3 $m^3/m^2/min$/ 68.9% |
| 2 inches from core | 118.0 $m^3/m^2/min$/ 64.6% | 117.1 $m^3/m^2/min$/ 63.7% | 116.4 $m^3/m^2/min$/ 65.6% |

The results listed in Table III indicate a similar trend across all three blends; the air permeabilities of the formed films tested decreased as the samples were taken from the outside of the rolls towards the cores, which correlates with the embossed thickness results. Overall, the air permeabilities ranged from about 115 m3/m2/min to about 185 m3/m2/min, depending on where the samples were taken, as well as the specific polymer blend used to extrude the initial polymer web.

Figure 14:
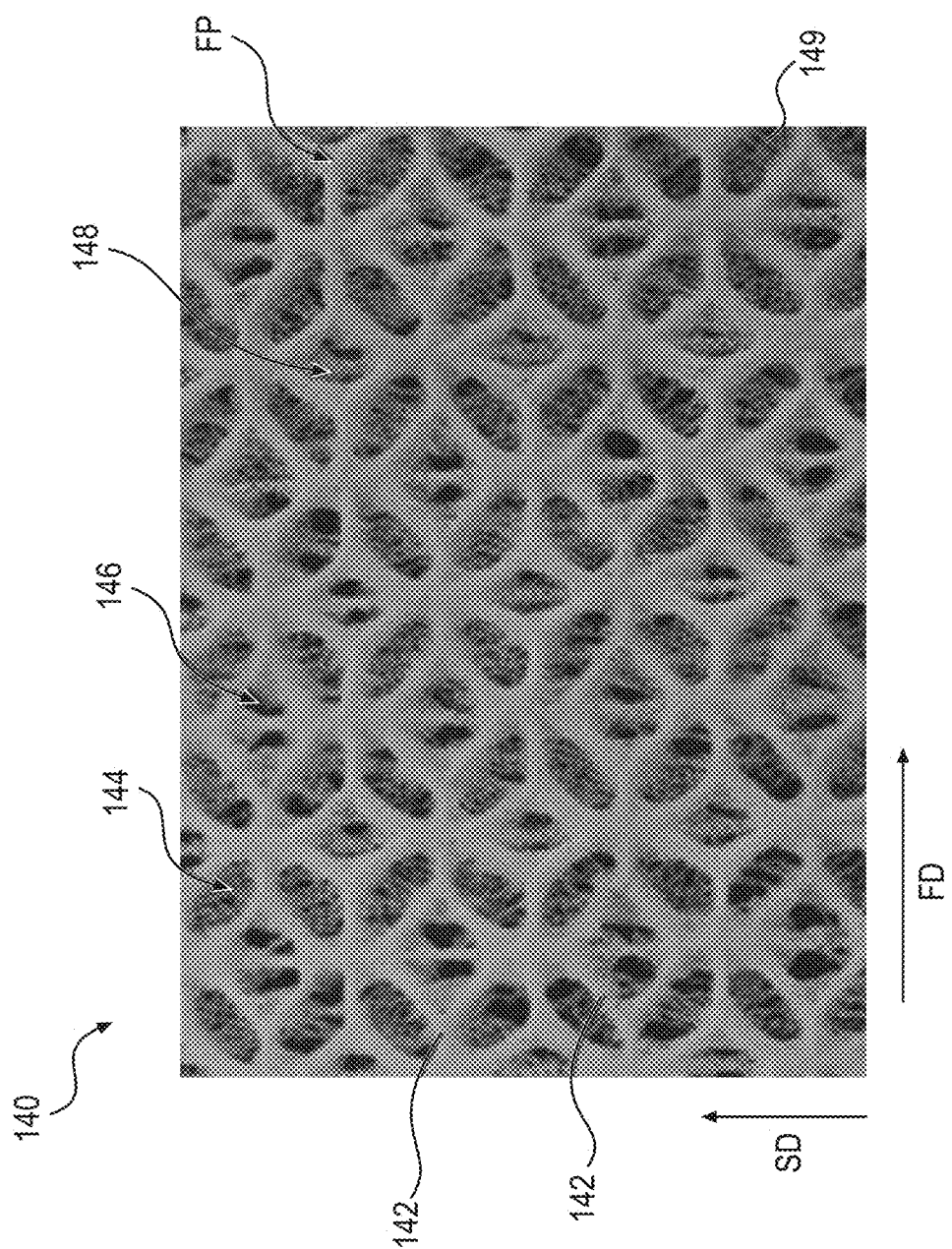
FIG. 14 is a top view of a portion of a formed film according to an embodiment of the present invention.

FIG. 14 illustrates an embodiment of a formed film 140 that includes raised areas that are generally shaped as ridges 142, portions of which are straight and portions of which are curved. The pattern of the ridges 142 defines gathering volumes of different sizes, including large gathering volumes 144, medium gathering volumes 146 and small gathering volumes 148. Four large gathering volumes 144 generally circumferentially surround one medium gathering volume 146, and four large gathering volumes 144 generally circumferentially surround one small gathering volume 148. Each of the gathering volumes 144, 146, 148 has a porous structure 149 at its bottom and the top of each gathering volume 144, 146, 148 is generally bound by the first plane FP in which tops of the ridges 142 are positioned. As illustrated, the medium gathering volumes 146 are generally aligned in a horizontal and vertical grid, and the small gathering volumes 148 are general aligned in a horizontal and vertical grid such that the medium and small gathering volumes alternate on diagonals. Generally straight raised ridges 142 connect corners of the medium gathering volumes 146 and the small gathering volumes 148 to provide additional strength to the formed film 140.

The design of the formed film 140 illustrated in FIG. 14 provides controlled collapse of the gathering volumes when the film is stretched in a first direction FD and a second direction SD. In the illustrated embodiment, the width of the small gathering volume 148 in the first direction FD is about 40-50% less than the width of the medium gathering volume 146 in the first direction FD, while the width of the small gathering volume 148 in the second direction SD is about the same as the width of the medium gathering volume 146 in the second direction SD. This design allows the small gathering volume 148 to collapse sooner than the medium gathering volume 146 when the formed film 140 is stretched in either the first direction FD or the second direction SD. "Collapse" as used herein refers to the raised areas and sidewalls extending therefrom surrounding the respective gathering channels moving towards each other to essentially decrease the size of the gathering volumes defined by the sidewalls. When the formed film 140 is stretched in either the first direction FD or the second direction SD, the large gathering volumes 144 tend to distort, but to a much lesser extent than the small and medium gathering volumes 148, 146.

Figure 15:
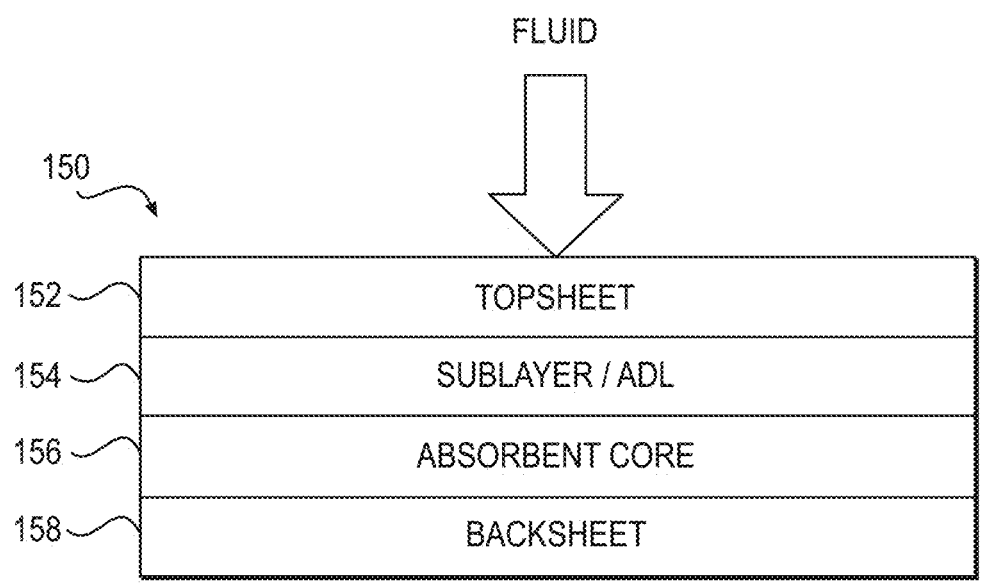
FIG. 15 is a schematic illustration of an absorbent article according to embodiments of the invention.

FIG. 15 is a schematic illustration of an absorbent article 150 according to embodiments of the invention. The absorbent article may be a feminine hygiene napkin, a baby diaper, or an adult incontinence product. As illustrated, the absorbent article 150 includes a topsheet 152, a sublayer 154, which may be an acquisition distribution layer ("ADL") or transfer layer located beneath the topsheet 152, an absorbent core 156 located beneath the sublayer 154, and a backsheet 158, which is impervious to fluids. The topsheet 152 and/or sublayer 154 may be one of the formed films described herein in accordance with embodiments of the invention.

The topsheet 152 is in contact with the user of the absorbent article 150 when worn by the user and fluid is received by the absorbent article 150 via the topsheet. Fluid that contacts the raised areas of the topsheet will move by capillary action to one of the gathering volumes and exit the topsheet through the porous structure located at the bottom of gathering volumes and in contact with the sublayer 154. The sublayer 154 may be a nonwoven material or another layer of a formed film. The sublayer 154 may be configured to distribute the fluid laterally and pass the fluid to the absorbent core 156. The backsheet 158 is in contact with an opposite side of the absorbent core 156 and is configured to keep the fluid from leaking out of the bottom side of the absorbent core 156 to the user's garment.

Although the formed films in accordance with embodiments of the invention may be used as topsheets in absorbent articles worn by end-users, the formed films in accordance with embodiments of the present invention may also function as sublayers (e.g. ADLs or transfer layers), in such absorbent articles. In other words, formed films in accordance with embodiments of the invention may provide the functionality of a traditional topsheet and/or a traditional sublayer. It is contemplated that formed films in accordance with embodiments of the invention may function as a combined topsheet/sublayer so that one layer of a traditional absorbent article that contains both a topsheet and sublayer may be eliminated.

Testing of Examples 1 and 2

Films representing Examples 1 and 2 described above, as well as two topsheets of the prior art, were tested for performance characteristics, including multiple strike through time, rewet, and softness. Feminine hygiene napkins sold under the brand name Equate™, and feminine hygiene napkins sold under the brand name U by Kotex® were deconstructed so that the topsheets were removed and only the chasses of the napkins were used. Formed films made in accordance with Example 1 and Example 2 described above were attached to the prior art chasses. In addition, first control samples were made with topsheets from the Equate napkin and second control samples were made with topsheets from the U by Kotex napkins.

Figure 16:
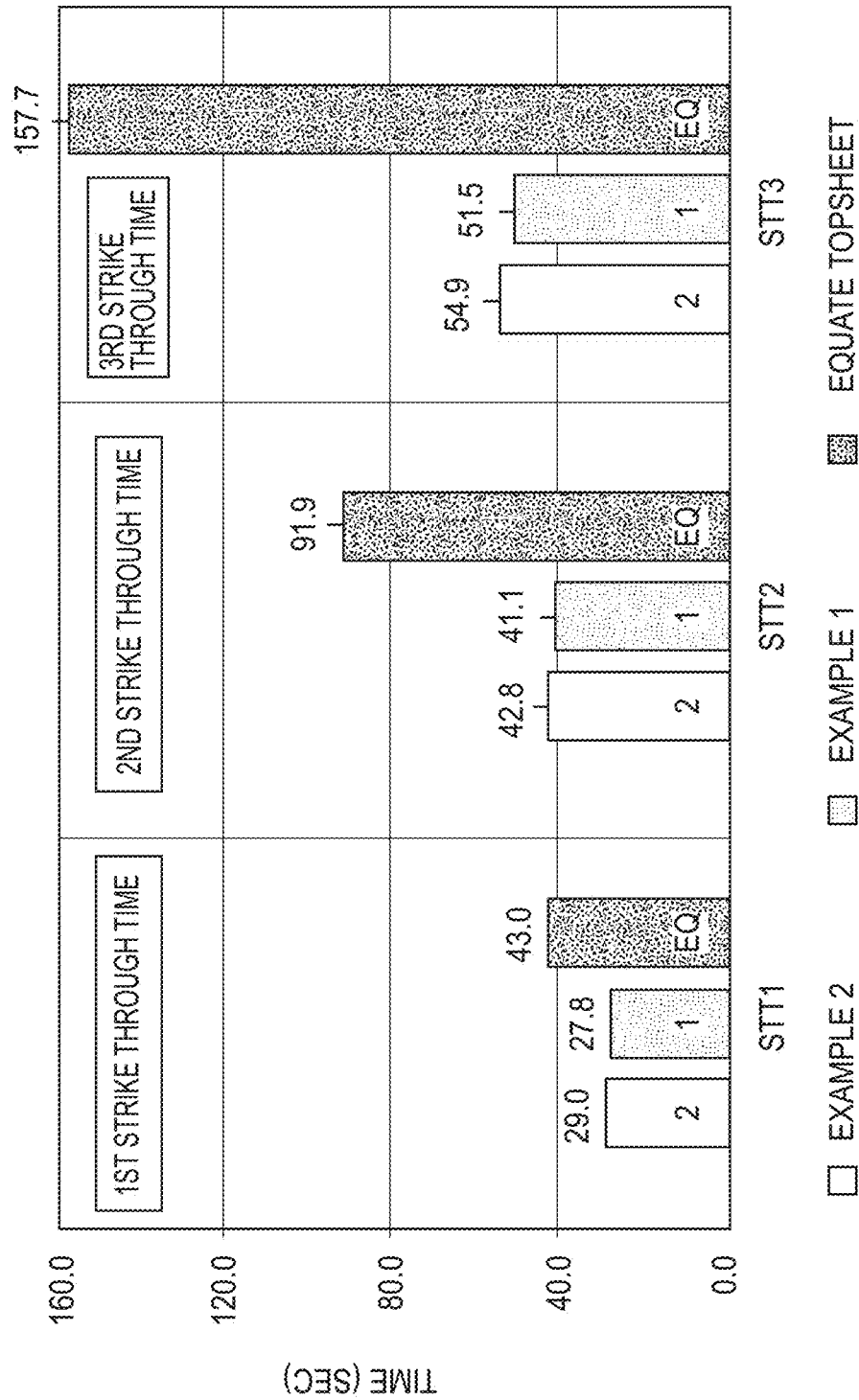
FIG. 16 is a graph summarizing test results of multiple strike through times with 4 ml of synthetic blood (11 cP) on a chassis of the prior art that compares embodiments of the present invention with a topsheet of the prior art.
Figure 17:
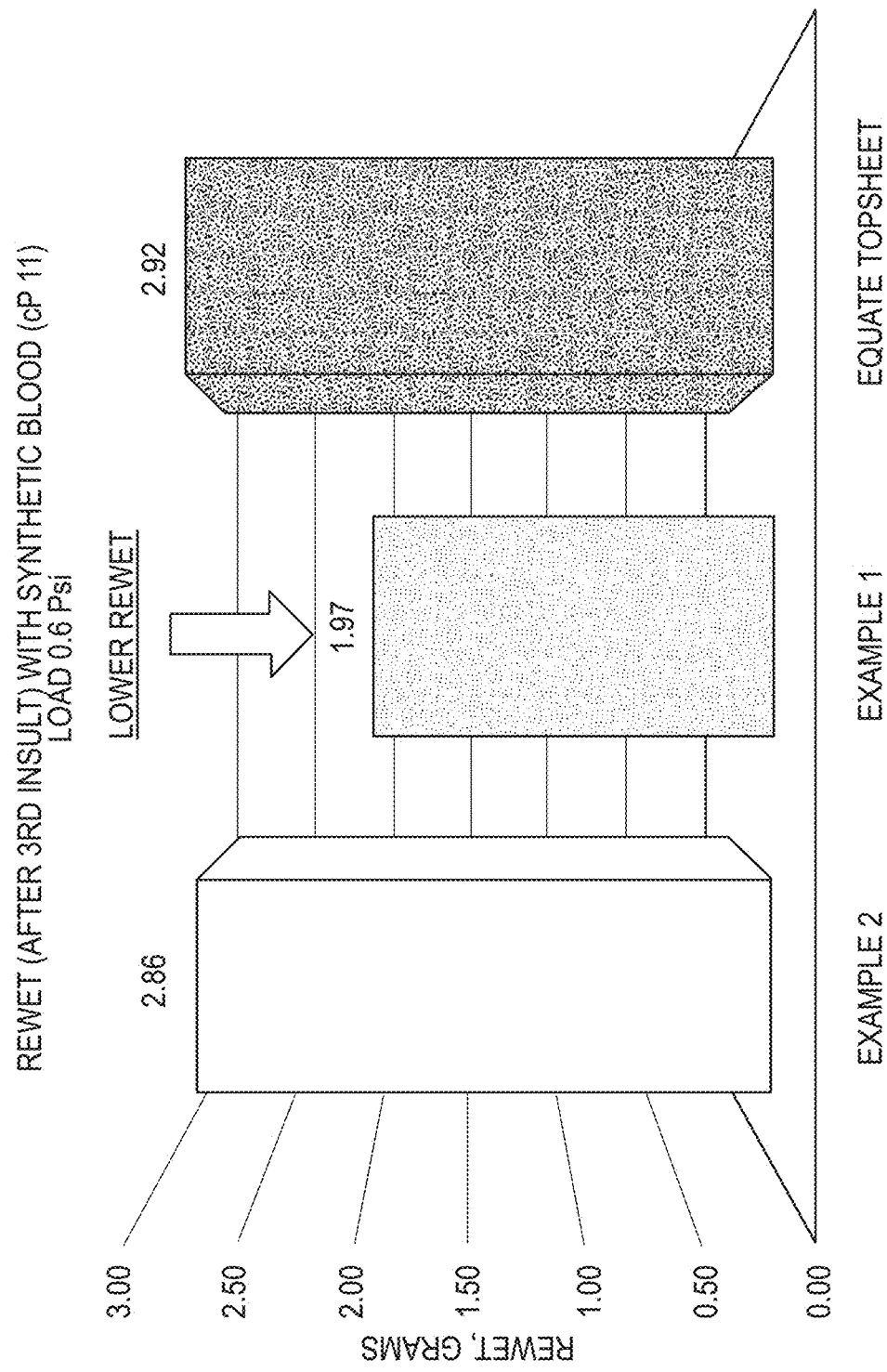
FIG. 17 is a graph summarizing test results of rewet after a third insult with synthetic blood (11 cP) on a chassis of the prior art that compares embodiments of the present invention with a topsheet of the prior art.

Each reconstructed napkin was insulted three times with 4 ml of synthetic blood (11 cP) at a rate of 10 ml/min. The strike through time after each insult was recorded and there was a waiting time of 10 minutes between each insult. The final rewet was measured at a pressure of 0.6 psi. FIG. 16 is a graph summarizing the results of the multiple strike through time test of the Example 1 topsheet, the Example 2 topsheet and the Equate topsheet on an Equate chassis, and FIG. 17 is a graph summarizing the results of the rewet test of the Example 1 topsheet, the Example 2 topsheet and the Equate topsheet on an Equate chassis. As illustrated in FIG. 16, both of the topsheets of the present invention (Example 1 and Example 2) were effective in reducing the acquisition time, as compared to the Equate topsheet. As illustrated in FIG. 17, a lower rewet was demonstrated by the Example 1 topsheet. The fibrillated structure of the Example 1 topsheet was able to minimize the amount of liquid returned to the surface, which resulted in a lower rewet. In addition, the pockets of the Example 1 topsheet allowed for fairly rapid acquisition, which resulted in a relatively fast strike through time.

Figure 18:
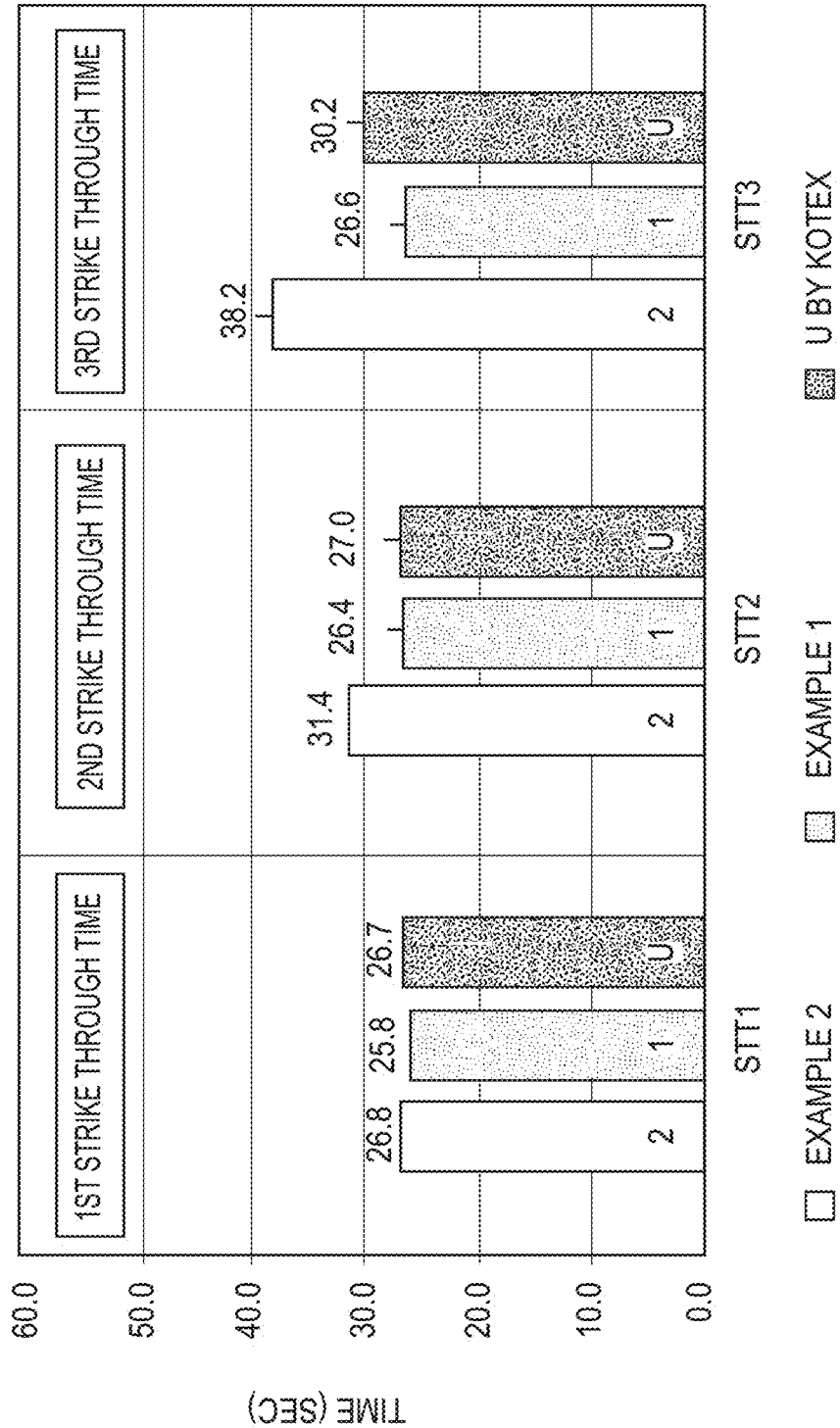
FIG. 18 is a graph summarizing test results of multiple strike through times with 4 ml of synthetic blood (11 cP) on a chassis of the prior art that compares embodiments of the present invention with a topsheet of the prior art.
Figure 19:
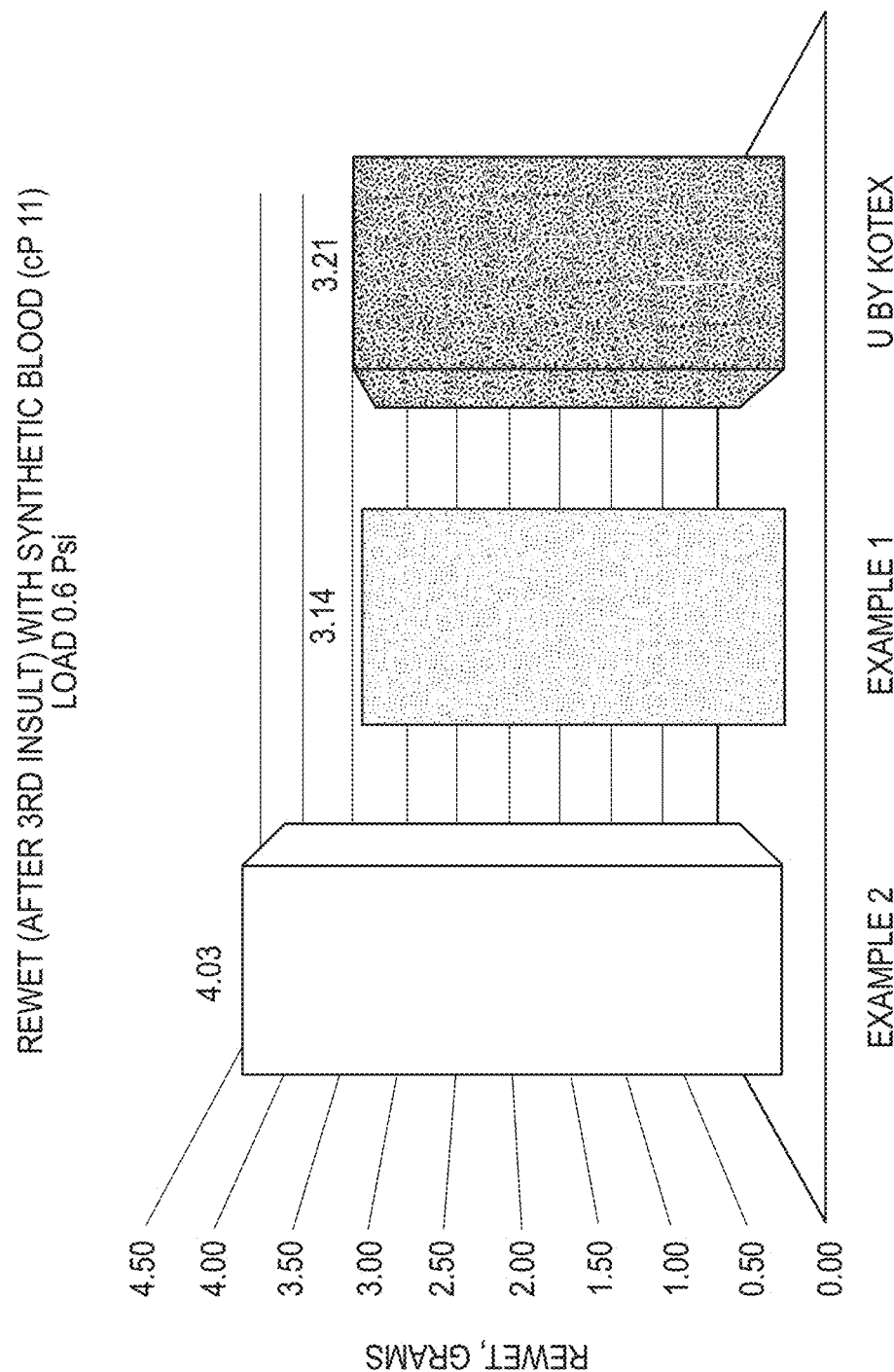
FIG. 19 is a graph summarizing test results of rewet after a third insult with synthetic blood (11 cP) on a chassis of the prior art that compares embodiments of the present invention with a topsheet of the prior art.

FIG. 18 is a graph summarizing the results of the multiple strike through time test of the Example 1 topsheet, the Example 2 topsheet and the U by Kotex topsheet on a U by Kotex chassis, and FIG. 19 is a graph summarizing the results of the rewet test of the Example 1 topsheet, the Example 2 topsheet and the U by Kotex topsheet on a U by Kotex chassis. As illustrated in FIG. 18, both of the topsheets of the present invention (Example 1 and Example 2) showed comparable performance to the U by Kotex topsheet. As illustrated in FIG. 19, the Example 1 topsheet demonstrated a rewet comparable to the U by Kotex topsheet. The fibrillated structure of the Example 1 topsheet was able to minimize the amount of liquid returned to the surface, even with a visible pattern.

Figure 20:
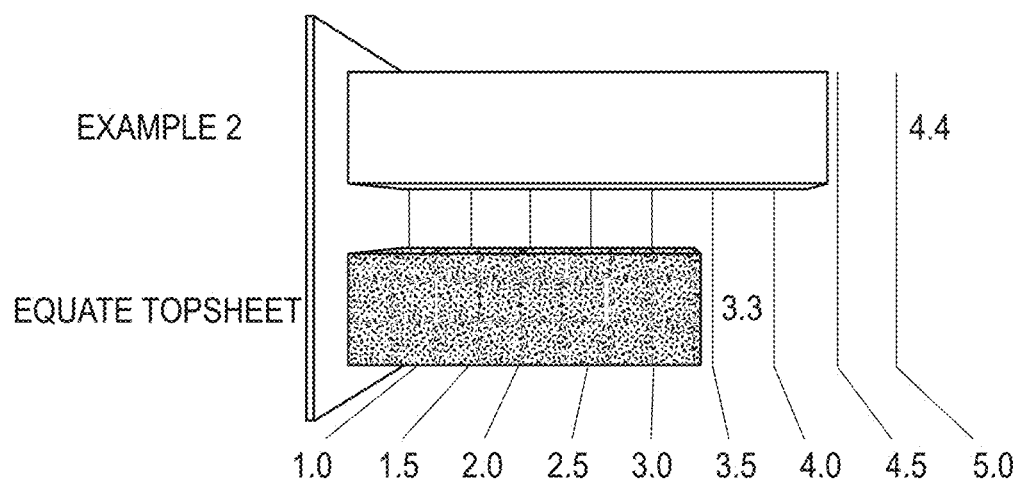
FIG. 20 is a graph summarizing results of a paired-comparison black box softness test between a formed film according to an embodiment of the invention and a topsheet of the prior art.
Figure 21:
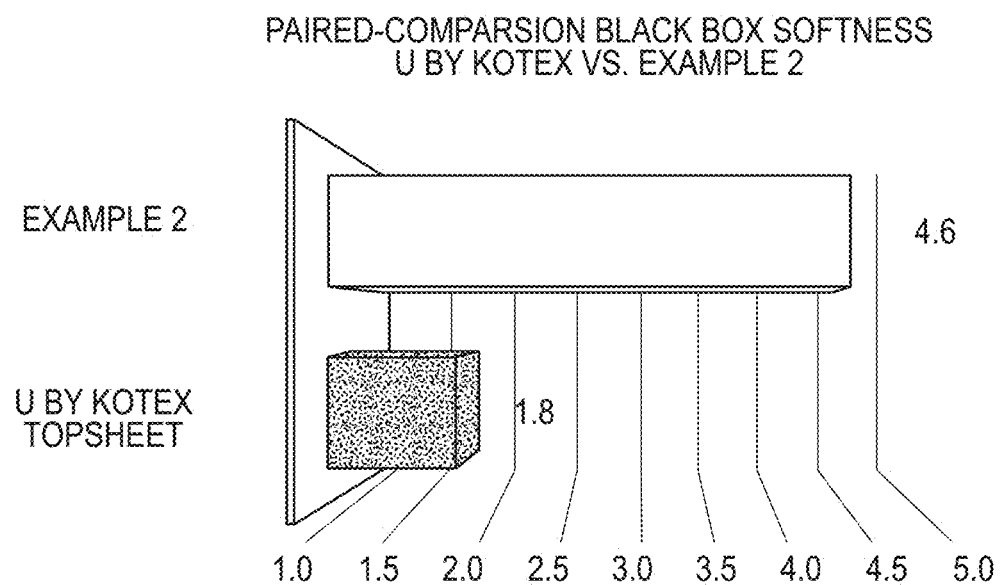
FIG. 21 is a graph summarizing results of a paired-comparison black box softness test between a formed film according to an embodiment of the invention and a topsheet of the prior art.

FIGS. 20 and 21 illustrate the results of a black box softness panel test that was conducted with a paired-comparison design. Example 1 and Example 2 topsheets were assembled into napkins, and the assembled napkins were each placed in a black box next to either a napkin assembled with the Equate topsheet or a napkin assembled with a U by Kotex topsheet. Eight panelists were asked to rate, on a scale of 1 (not soft) to 5 (very soft), each sample in the black box without looking at the samples. FIG. 20 illustrates the results of the Example 2 topsheet versus the Equate topsheet, and FIG. 21 illustrates the results of the Example 2 topsheet versus the U by Kotex topsheet. For each pairing, the Example 2 topsheet rated higher (more soft) than the prior art topsheet.

Testing of Examples 1, 3, 4 and 5

Films representing Examples 1, 3, 4 and 5 described above, as well as two topsheets of the prior art, were tested for performance characteristics, including multiple strike through time, rewet, and run-off. Feminine hygiene napkins sold by Unicharm were deconstructed so that the topsheets were removed and only the chasses of the napkins were used. Formed films made in accordance with Examples 1, 3, 4 and 5 described above were attached to the prior art chasses. In addition, first control samples were made with a prior art formed film topsheet (Control 1) and second control samples were made with the nonwoven topsheet that had been removed from the Unicharm napkins (Control 2).

Figure 22:
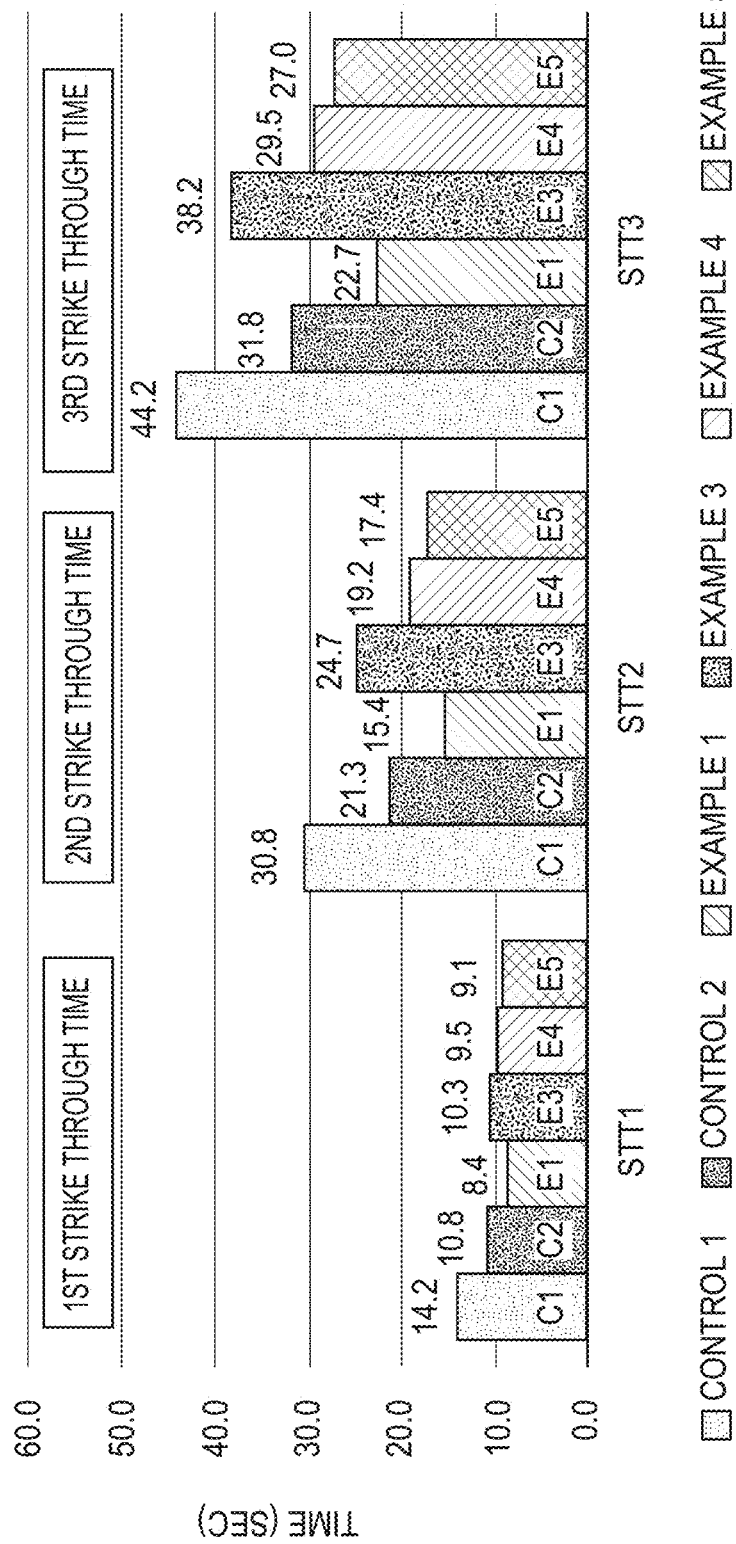
FIG. 22 is a graph summarizing test results of multiple strike through times with 4 ml of synthetic blood (11 cP) on a chassis of the prior art that compares embodiments of the present invention with two topsheets of the prior art.
Figure 23:
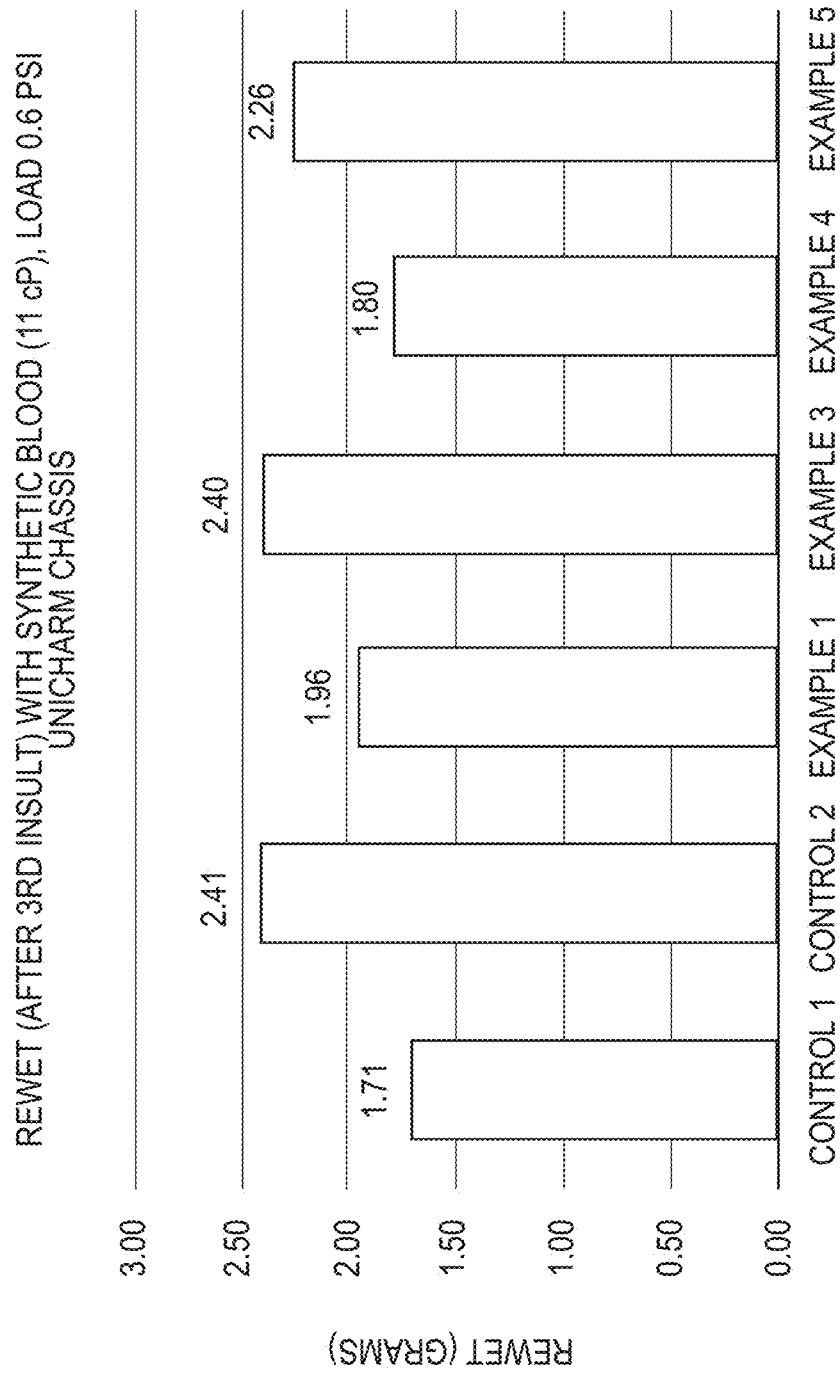
FIG. 23 is a graph summarizing test results of rewet after a third insult with synthetic blood (11 cP) on a chassis of the prior art that compares embodiments of the present invention with two topsheets of the prior art.
Figure 24:
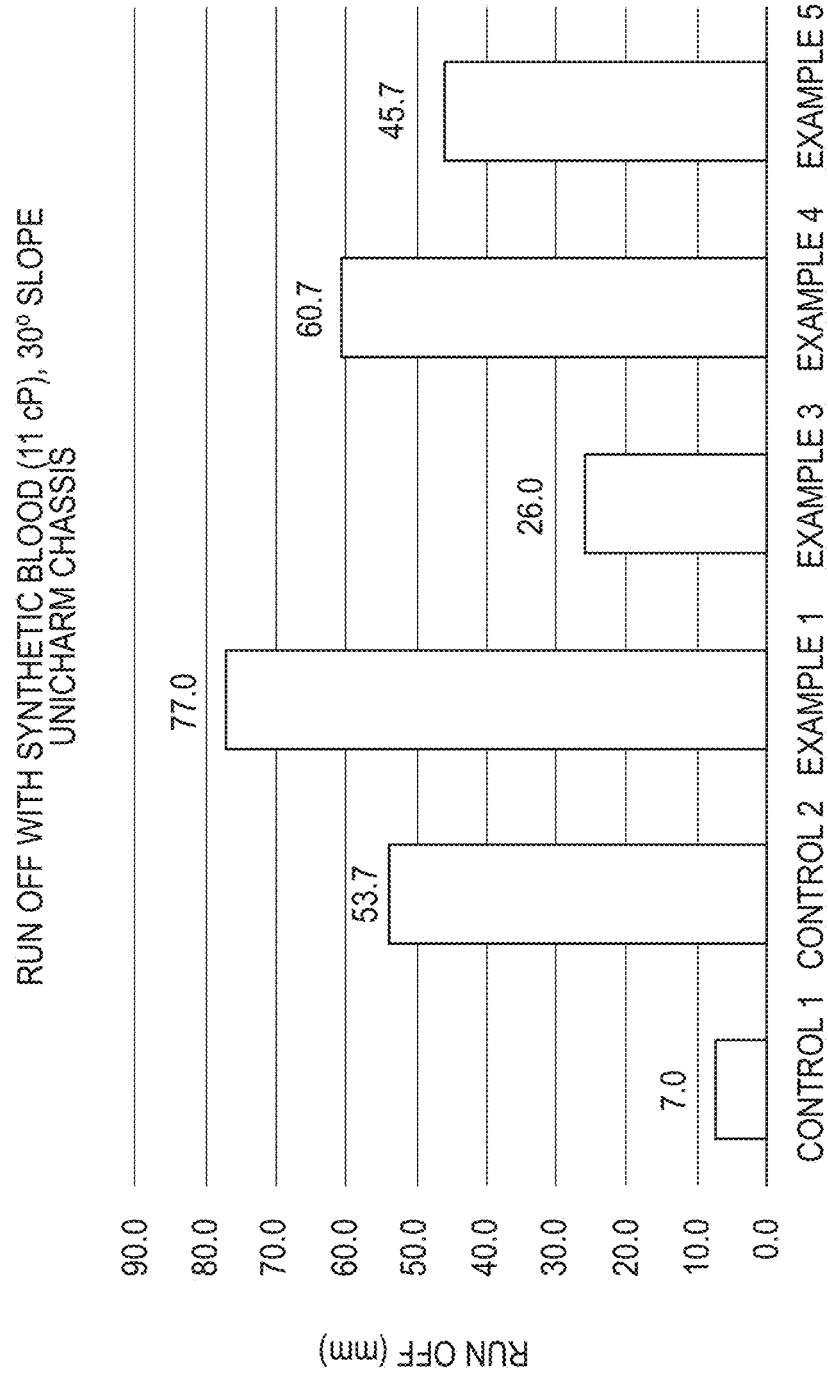
FIG. 24 is a graph summarizing test results of run off with synthetic blood (11 cP) on a chassis of the prior art oriented on a 30° slope that compares embodiments of the present invention with two topsheets of the prior art.

Each reconstructed napkin was insulted three times with 4 ml of synthetic blood (11 cP) at a rate of 10 ml/min. The strike through time after each insult was recorded and there was a waiting time of 5 minutes between each insult. The final rewet was measured at a pressure of 0.6 psi. FIG. 22 is a graph summarizing the results of the multiple strike through time test and FIG. 23 is a graph summarizing the results of the rewet test of the Control 1 and 2 topsheets, and the Example 1, 3, 4 and 5 topsheets on the Unicharm chassis. In addition, a run-off test was completed by dispensing 10 ml of synthetic blood (11 cP) for 15 seconds with a pump onto each reconstructed napkin that was oriented on a 30° slope. The distance between the distal edge of the stain created by the synthetic blood and the distal edge of the napkin was measured for each sample. FIG. 24 is a graph summarizing the results of the run-off test of the Control 1 and 2 topsheets, and the Example 1, 3, 4 and 5 topsheets on the Unicharm chassis.

As illustrated in FIG. 22, the Example 1, 4 and 5 topsheets of the present invention were effective in reducing the acquisition time, as compared to the prior art topsheets. As illustrated in FIG. 23, a lower rewet was demonstrated by the Example 1, 4 and 5 topsheets as compared to the Unicharm nonwoven topsheet (Control 2). The porous or fibrillated structure (fibrous net) in the porous structures or pockets (gathering channels) of the Example 1, 4 and 5 topsheets was able to minimize the amount of liquid that returned to the top surface, which resulted in a lower rewet as compared to the Unicharm nonwoven topsheet (control 2). In addition, the pockets of the Example 1, 4 and 5 topsheets allowed for fairly rapid acquisition, which resulted in a relatively fast strike through time. In the run-off test, all of the samples that were tested had an absorbency of greater than 99%. As illustrated in FIG. 24, the Example 1, 3, 4 and 5 topsheets performed better than the prior art formed film topsheet (Control 1), and the Example 1 and 4 topsheets performed better than the Unicharm nonwoven topsheet (Control 2), indicating that the large pockets (gathering volumes) were effective in acquiring the fluid and transferring the fluid into the absorbent core.

Testing of Examples 3, 4 and 5

Films representing Examples 3, 4 and 5 described above, as well as two topsheets of the prior art, were tested for multiple strike through time, rewet, and run-off using a different napkin chassis. Feminine hygiene napkins sold under the brand name Space 7 by Hengan were deconstructed so that the topsheets were removed and only the chasses of the napkins were used. Formed films made in accordance with Examples 3, 4 and 5 described above were attached to the prior art chasses. In addition, first control samples were made with a prior art formed film topsheet (the same topsheet that was used on the Unicharm chassis described above, i.e. Control 1) and second control samples were made with the nonwoven topsheet (Control 3) that had been removed from the Hengan napkins.

Figure 25:
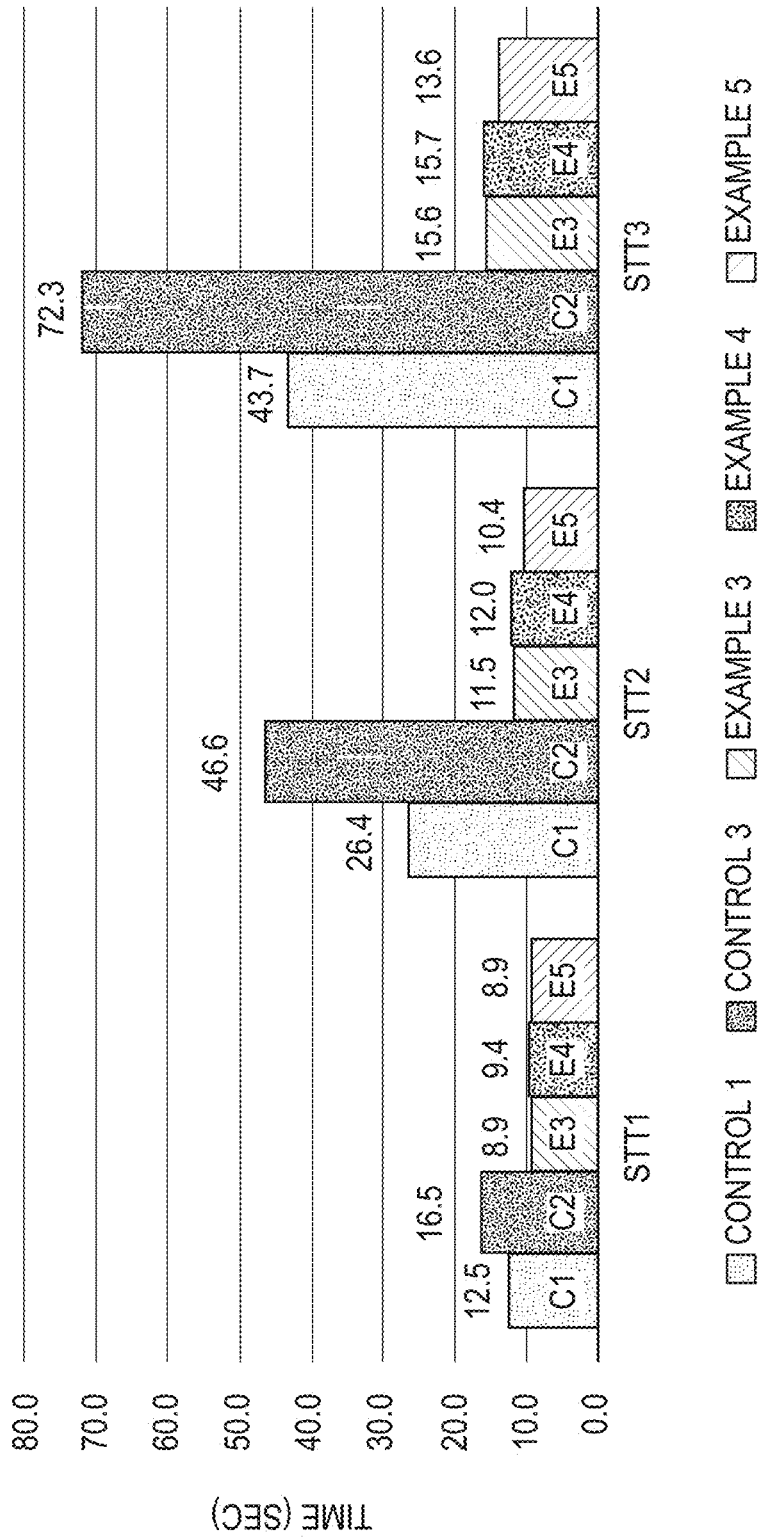
FIG. 25 is a graph summarizing test results of multiple strike through times with 4 ml of synthetic blood (11 cP) on a chassis of the prior art that compares embodiments of the present invention with two topsheets of the prior art.
Figure 26:
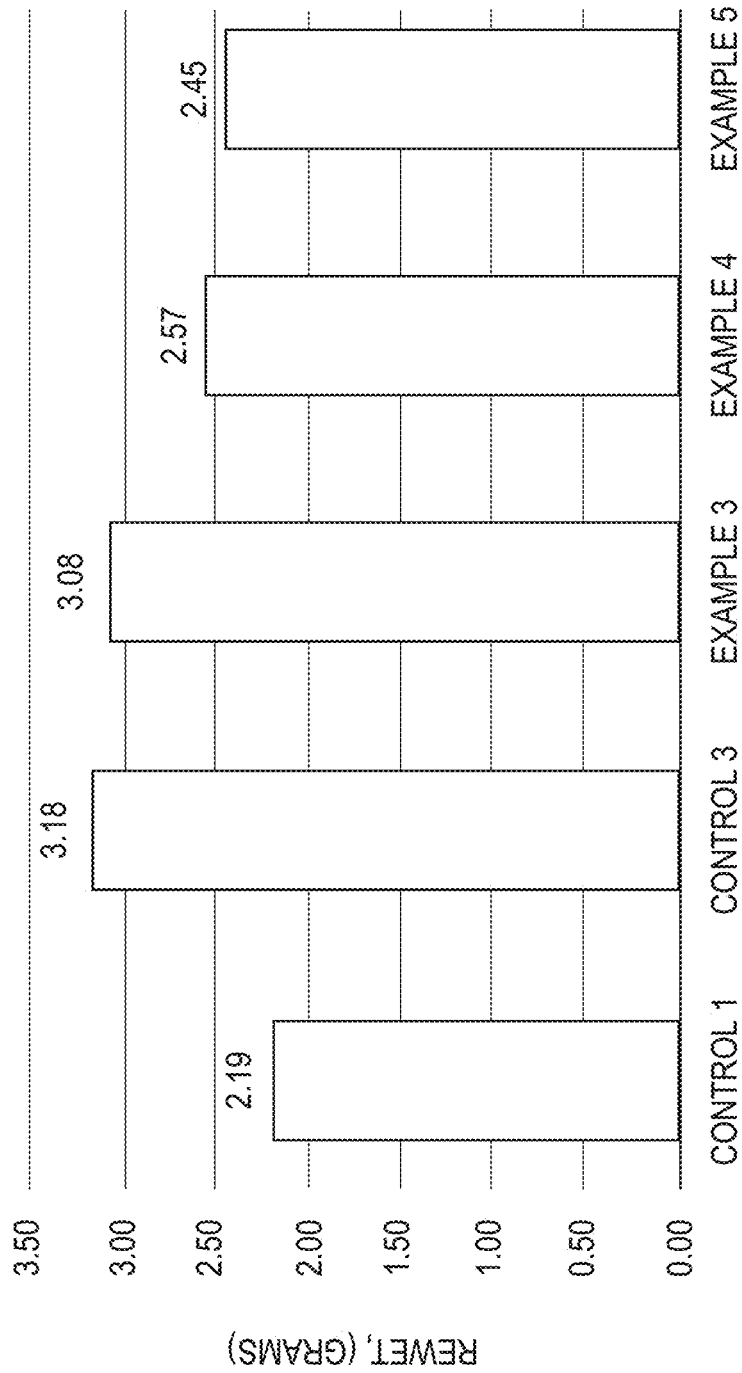
FIG. 26 is a graph summarizing test results of rewet after a third insult with synthetic blood (11 cP) on a chassis of the prior art that compares embodiments of the present invention with two topsheets of the prior art.
Figure 27:
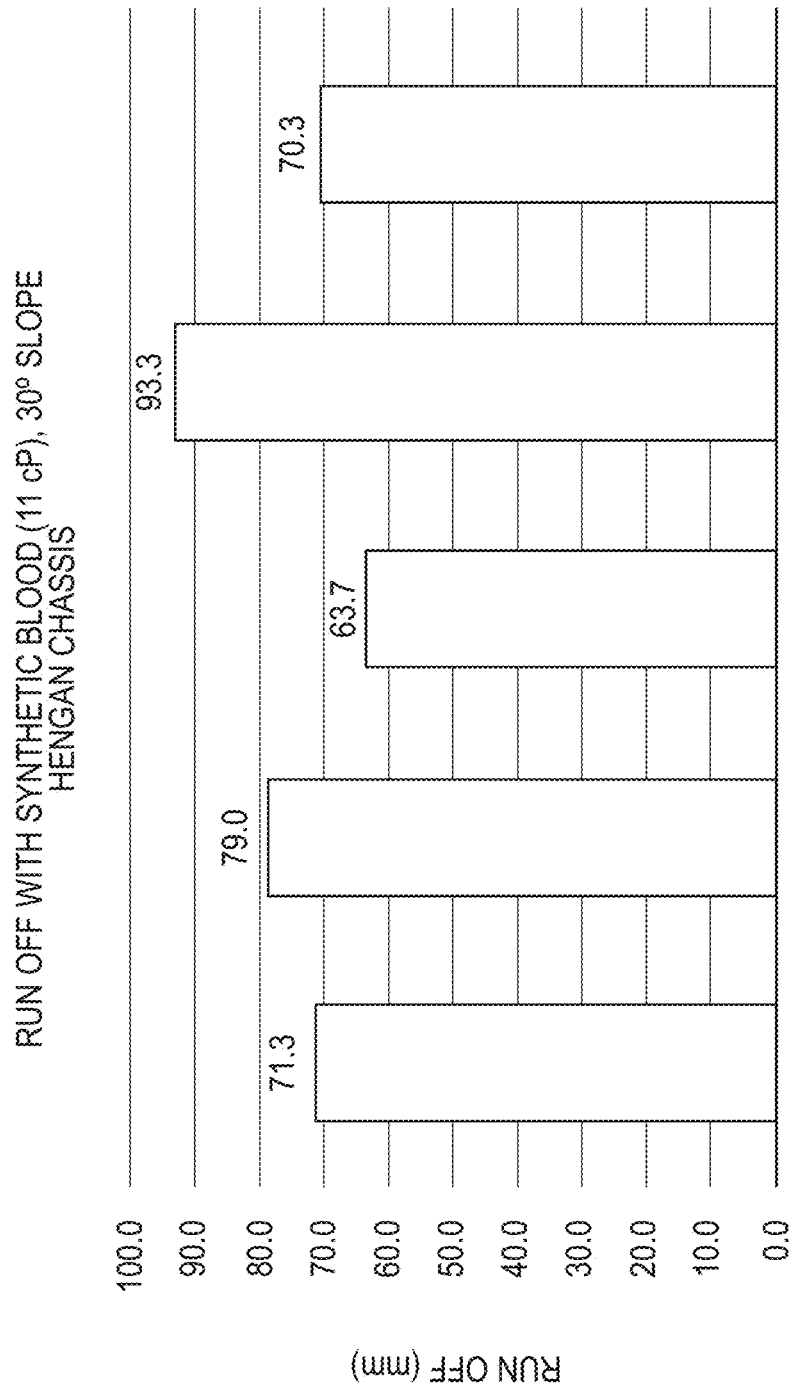
FIG. 27 is a graph summarizing test results of run off with synthetic blood (11 cP) on a chassis of the prior art oriented on a 30° slope that compares embodiments of the present invention with two topsheets of the prior art.
Figure 28:
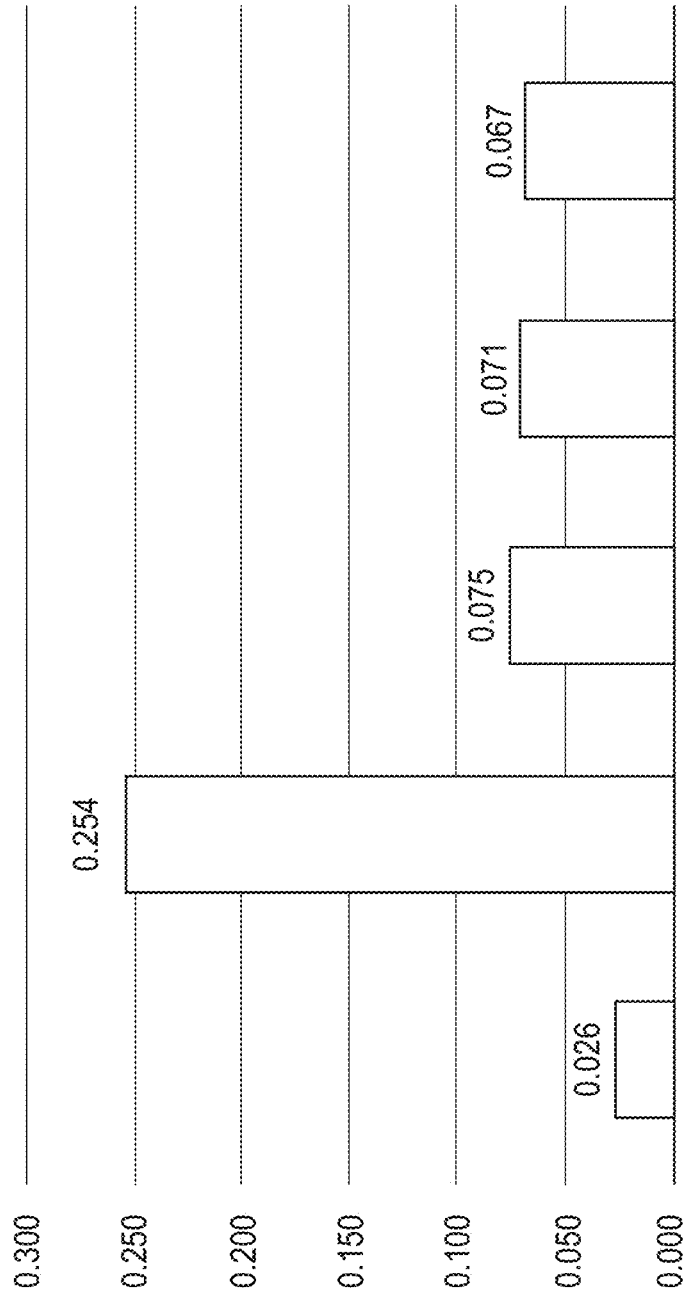
FIG. 28 is a graph summarizing test results of wetness transferred to pick-up paper with synthetic blood (11 cP) under 0.13 psi after 5 minutes on a chassis of the prior art that compares embodiments of the present invention with two topsheets of the prior art.

Each reconstructed napkin was insulted three times with 4 ml of synthetic blood (11 cP) at a rate of 10 ml/min. The strike through time after each insult was recorded and there was a waiting time of 5 minutes between each insult. The final rewet was measured at a pressure of 0.6 psi. FIG. 25 is a graph summarizing the results of the multiple strike through time test and FIG. 26 is a graph summarizing the results of the rewet test of the Control 1 and 3 topsheets, and the Example 3, 4 and 5 topsheets on the Hengan chassis. In addition, a run-off test was completed by dispensing 10 ml of synthetic blood (11 cP) for 15 seconds with a pump onto each reconstructed napkin that was oriented on a 30° slope. The distance between the distal edge of the stain created by the synthetic blood and the distal edge of the napkin was measured for each sample. FIG. 27 is a graph summarizing the results of the run-off test of the two control topsheets, and the Example 3, 4 and 5 topsheets on the Hengan chassis. In addition, a wetness test was completed by dispensing 10 ml of synthetic blood (11 cP) for 15 seconds with a pump onto each reconstructed napkin and after 5 minutes, a pressure of 0.13 psi was applied to the reconstructed napkin for 15 seconds and the wetness transferred onto a pick-up paper was measured. FIG. 28 is a graph summarizing the results of the wetness test of the Control 1 and 2 topsheets, and the Example 3, 4 and 5 topsheets.

As illustrated in FIG. 25, the Example 3, 4 and 5 topsheets of the present invention were effective in reducing the acquisition time, as compared to the prior art topsheets. As illustrated in FIG. 26, a lower rewet was demonstrated by the Example 3, 4 and 5 topsheets as compared to the Hengan nonwoven topsheet (Control 3). The fibrillated structure (fibrous net) in the pockets (gathering channels or volumes) of the Example 1, 4 and 5 topsheets was able to minimize the amount of liquid that returned to the surface, which resulted in a lower rewet as compared to the Hengan nonwoven topsheet (Control 3). In addition, the pockets of the Example 4 and 5 topsheets allowed for fairly rapid acquisition, which resulted in a relatively fast strike through time. In the run-off test, all of the samples that were tested had an absorbency of greater than 99%. As illustrated in FIG. 27, the Example 4 topsheet performed better than the prior art formed film topsheet (Control 1) and the Hengan nonwoven topsheet (Control 3), indicating that the pockets were effective in acquiring the fluid and transferring the fluid into the absorbent core. As illustrated in FIG. 28, the Example 3, 4 and 5 topsheets showed surface wetness comparable to the prior art formed film topsheet (Control 1).

Formed films in accordance with embodiments of the invention may be manufactured using thermoforming processes, including but not limited to vacuum forming, hydroforming, mechanical forming, embossing, and/or combinations thereof. Preferably, the formed films in accordance with embodiments of the invention are manufactured using a hydro-forming process and apparatus 400 illustrated in FIG. 4, for example.

Embodiments of the present invention described above may also provide a formed film that includes a first surface generally located in a first plane, a second surface generally located in a second plane parallel to and spaced from the first plane, a third surface generally located in a third plane parallel to and spaced from the first plane and the second plane, in between the first plane and the second plane, a fibrillated structure extending between the second surface and the third surface, and a plurality of ridges having sidewalls extending between the first surface and the third surface, and top portions defining the first surface. The plurality of sidewalls and the fibrillated structure define a plurality of pockets relative to the first surface.

Embodiments of the present invention described above may also provide a formed film that includes a web of material comprising a plurality of micro-apertures formed therein. The web of material has a first surface generally located in a first plane, a second surface generally located in a second plane parallel to and spaced from the first plane, a third surface generally located in a third plane parallel to and spaced from the first plane and the second plane, in between the first plane and the second plane, and a plurality of grooves extending from the first surface to the third surface. Bottoms of the grooves are generally located in the third plane. The web of material also includes a plurality of macro-apertures extending from the third surface to the second surface. The plurality of grooves and the macro-apertures define a plurality of raised areas relative to the bottoms of the grooves and the macro-apertures. The raised areas have tops that generally define the first surface.

The embodiments described herein represent a number of possible implementations and examples and are not intended to necessarily limit the present disclosure to any specific embodiments. Instead, various modifications can be made to these embodiments as would be understood by one of ordinary skill in the art. Any such modifications are intended to be included within the spirit and scope of the present disclosure and protected by the following claims.

What is claimed is:

1. A formed film comprising:
a first surface generally located in a first plane;
a second surface generally located in a second plane parallel to and spaced from the first plane;
a third surface generally located in a third plane parallel to and spaced from the first plane and the second plane, in between the first plane and the second plane;
a porous structure extending vertically between the second surface and the third surface; and
a plurality of raised areas having sidewalls extending between the first surface and the third surface, and top portions defining the first surface, the plurality of sidewalls, the porous structure and the first plane defining a plurality of gathering volumes,
wherein the plurality of raised areas comprise a plurality of micro-apertures, and
wherein the porous structure comprises a fibrillated structure.

2. The formed film according to claim 1, wherein the micro-apertures are arranged in a 40 to 120 mesh pattern.

3. The formed film according to claim 2, wherein the micro-apertures are arranged in an 80 mesh pattern.

4. The formed film according to claim 2, wherein the micro-apertures are arranged in a 100 mesh pattern.

5. The formed film according to claim 1, wherein a distance between the first plane and the second plane is between about 500 μm and about 1200 μm.

6. The formed film according to claim 5, wherein the distance between the first plane and the second plane is between about 500 μm and about 1000 μm.

7. The formed film according to claim 6, wherein the distance between the first plane and the second plane is between about 600 μm and about 900 μm.

8. The formed film according to claim 1, wherein the raised areas are ridges.

9. The formed film according to claim 8, wherein the ridges are generally straight.

10. The formed film according to claim 8, wherein the ridges are generally curved.

11. The formed film according to claim 1, wherein the raised areas form a plurality of spirals.

12. The formed film according to claim 1, wherein the formed film comprises three layers, including a core layer and two skin layers on opposite sides of the core layer.

13. The formed film according to claim 1, wherein the gathering volumes are pockets.

14. The formed film according to claim 1, wherein the gathering volumes are channels.

15. An absorbent article comprising:
a topsheet configured to contact skin of a user of the absorbent article when the absorbent article is worn by the user, the topsheet comprising a formed film, the formed film comprising
a first surface generally located in a first plane, a second surface generally located in a second plane parallel to and spaced from the first plane, a third surface generally located in a third plane parallel to and spaced from the first plane and the second plane, in between the first plane and the second plane, a porous structure extending vertically between the second surface and the third surface, and a plurality of raised areas having sidewalls extending between the first surface and the third surface, and top portions defining the first surface, the plurality of sidewalls, the porous structure and the first plane defining a plurality of gathering volumes;

a liquid impervious backsheet configured to be in contact with a garment worn by the user; and an absorbent core positioned in between the topsheet and the backsheet, wherein the plurality of raised areas comprise a plurality of micro-apertures, and wherein the porous structure comprises a fibrillated structure.

16. The absorbent article according to claim 15, further comprising a sublayer positioned in between the topsheet and the absorbent core.

\* \* \* \* \*